(12) United States Patent
Kuwahara et al.

(10) Patent No.: US 8,853,373 B2
(45) Date of Patent: Oct. 7, 2014

(54) METHOD AND REAGENT FOR GENE SEQUENCE ANALYSIS

(75) Inventors: Masayasu Kuwahara, Kiryu (JP); Tomoharu Kajiyama, Higashiyamato (JP); Hideki Kambara, Hachioji (JP)

(73) Assignees: Hitachi, Ltd., Tokyo (JP); National University Corporation Gunma University, Gunma (JP)

( * ) Notice: Subject to any disclaimer, the term of this patent is extended or adjusted under 35 U.S.C. 154(b) by 88 days.

(21) Appl. No.: 13/389,842

(22) PCT Filed: Aug. 10, 2010

(86) PCT No.: PCT/JP2010/063529
§ 371 (c)(1),
(2), (4) Date: Feb. 10, 2012

(87) PCT Pub. No.: WO2011/019031
PCT Pub. Date: Feb. 17, 2011

(65) Prior Publication Data
US 2012/0270210 A1 Oct. 25, 2012

(30) Foreign Application Priority Data
Aug. 14, 2009 (JP) ................................. 2009-187917

(51) Int. Cl.
*C07H 17/00* (2006.01)
*C07H 21/02* (2006.01)
*C12Q 1/68* (2006.01)
*C12P 19/34* (2006.01)

(52) U.S. Cl.
USPC ............ 536/4.1; 536/23.1; 435/6.1; 435/91.1

(58) Field of Classification Search
USPC ........................... 536/4.1, 23.1; 435/6.1, 91.1
See application file for complete search history.

(56) References Cited

U.S. PATENT DOCUMENTS 7,459,311 B2 12/2008 Nyren et al.
2007/0166729 A1 7/2007 Kambara et al.

FOREIGN PATENT DOCUMENTS

| JP | 2001-501092 | 1/2001 |
|---|---|---|
| JP | 2002-193991 | 10/2002 |
| JP | 2004-508054 | 3/2004 |
| JP | 2007-56001 | 3/2007 |
| JP | 2007-97471 | 4/2007 |
| JP | 2009-516749 | 4/2009 |
| WO | WO 98/13523 A1 | 4/1998 |
| WO | WO 98/28440 A1 | 7/1998 |
| WO | WO 2007/062160 | 5/2007 |
| WO | WO 2008/144315 A1 | 11/2008 |

OTHER PUBLICATIONS

Jager et al. JACS 2005, 127, 15071-15082.*

(Continued)

*Primary Examiner* — Jezia Riley
(74) *Attorney, Agent, or Firm* — Antonelli, Terry, Stout & Kraus, LLP.

(57) ABSTRACT

Provided is a nucleic acid substrate which has nucleic acid substrate characteristics equivalent to those of dATP, has a low substrate specificity for luciferase, exerts no negative effect on enzymatic reactions such as a complementary-strand synthesis, and therefore is particularly suitable for the pyrosequencing method. As a nucleic acid substrate complementary to nucleotide T, a 7-substituted deoxyribonucleotide triphosphate whose 7-position of a purine group is modified by a substituent is used as a substitute for a nucleotide α-thiotriphosphate analog.

6 Claims, 20 Drawing Sheets

(56) References Cited

OTHER PUBLICATIONS

Communication issued by the Japan Patent Office in regards to Japanese application JP-2001-526764 2013.
Japanese Official Action dated Aug. 6, 2013, for JP Application No. 2011-526764.
Masayasu Kuwahara et al., Substrate property and incorporation accuracy of various dATP analogs during enzymatic polymerization using thermostable DNA polymerases, Nucleic Acids Symposium Series No. 50, pp. 31-32. 2006.
Jonas Eriksson et al., 7-Deaza-2'-Deoxyadenosine-5'-triphosphate as an Alternative Nucleotide for the Pyrosequencing Technolgoy, Nucleosides, Nucleotides & Nucleic Acids, 2004, pp. 1583-1594, vol. 23, No. 10.
Anders Hanning et al., Laser-induced Fluorescence detection by Liquid Core Waveguiding Applied to DNA Sequencing by Capillary Electrophoresis, analytical Chemistry, Aug. 1, 2000, pp. 3423-3430, vol. 72, No. 15.
Baback Gharizadeh et al., Long-read Pyrosequencing Using Pure 2'-Deoxyadenosine-5'-0'-(1-thiotriphosphate) Sp-isomer, Analytical Biochemistry 301, 2002, pp. 82-90.

\* cited by examiner

Fig. 1
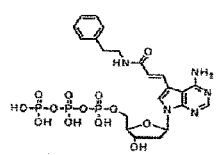
A3a
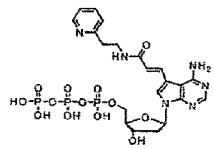
A3b
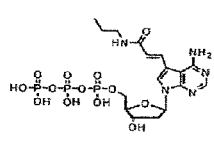
A3c
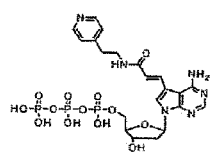
A3d
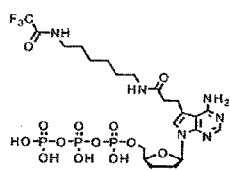
B3
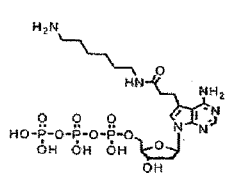
B4
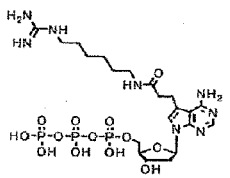
B5
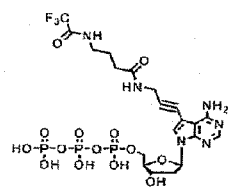
C2
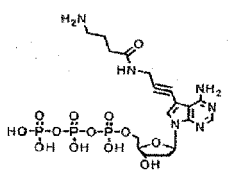
C3
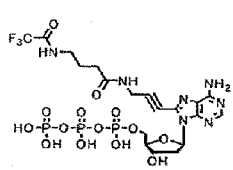
D2
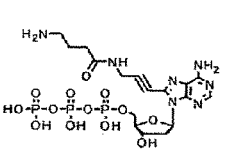
D3

Fig. 12
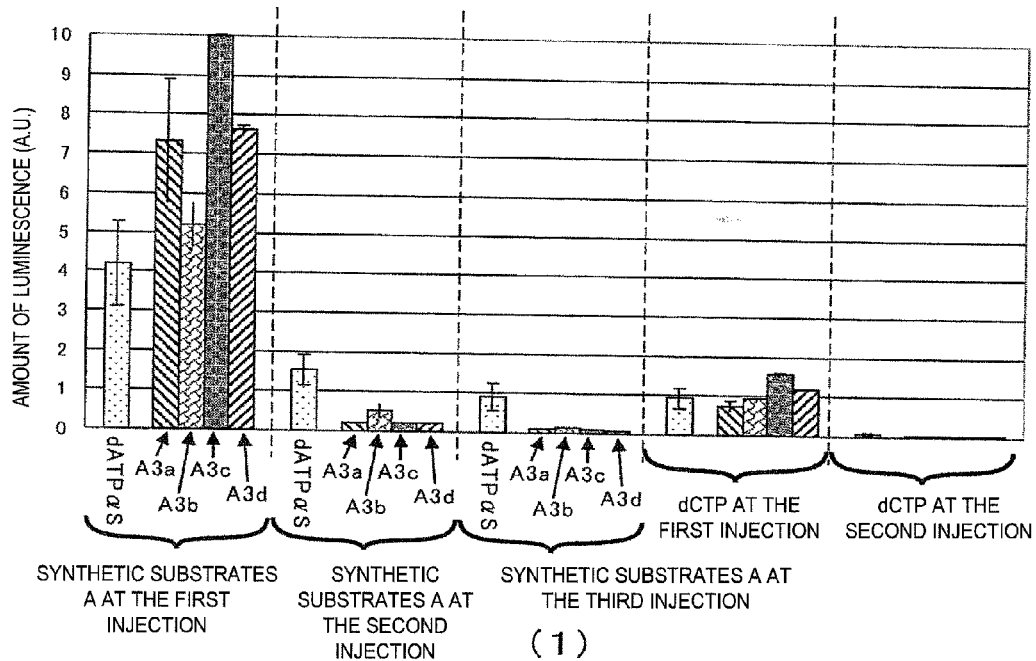
(1)
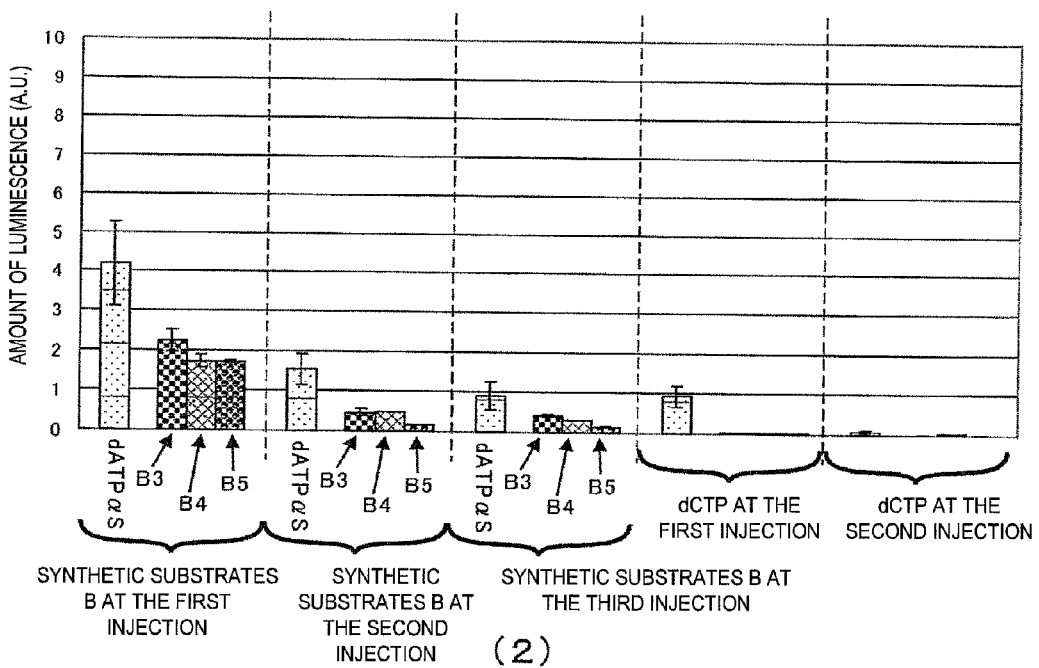
(2)

SEQUENCE LISTING

```
<160> NUMBER OF SEQ ID NOS: 10

<210> SEQ ID NO 1
<211> LENGTH: 71
<212> TYPE: DNA
<213> ORGANISM: Artificial
<220> FEATURE:
<223> OTHER INFORMATION: Synthetic DNA

<400> SEQUENCE: 1
gactgaatat aaacttgtgg tagttggagc tgttggcgta ggcaagagtg ccttgacgat      60
acagctaatt c                                                          71

<210> SEQ ID NO 2
<211> LENGTH: 71
<212> TYPE: DNA
<213> ORGANISM: Artificial
<220> FEATURE:
<223> OTHER INFORMATION: Synthetic DNA

<400> SEQUENCE: 2
gactgaatat aaacttgtgg tagttggagc tagtggcgta ggcaagagtg ccttgacgat      60
acagctaatt c                                                          71

<210> SEQ ID NO 3
<211> LENGTH: 71
<212> TYPE: DNA
<213> ORGANISM: Artificial
<220> FEATURE:
<223> OTHER INFORMATION: Synthetic DNA

<400> SEQUENCE: 3
gactgaatat aaacttgtgg tagttggagc tgctggcgta ggcaagagtg ccttgacgat      60
acagctaatt c                                                          71

<210> SEQ ID NO 4
<211> LENGTH: 71
<212> TYPE: DNA
<213> ORGANISM: Artificial
<220> FEATURE:
<223> OTHER INFORMATION: Synthetic DNA

<400> SEQUENCE: 4
gactgaatat aaacttgtgg tagttggagc tgatggcgta ggcaagagtg ccttgacgat      60
acagctaatt c                                                          71

<210> SEQ ID NO 5
<211> LENGTH: 29
<212> TYPE: DNA
<213> ORGANISM: Artificial
<220> FEATURE:
<223> OTHER INFORMATION: Synthetic DNA

<400> SEQUENCE: 5
acgttttttg gcgtaggcaa gagtgcctt                                        29
```

<210> SEQ ID NO 6
<211> LENGTH: 21
<212> TYPE: DNA
<213> ORGANISM: Artificial
<220> FEATURE:
<223> OTHER INFORMATION: Synthetic DNA

<400> SEQUENCE: 6
aaggcactct tgcctacgcc a                                              21

<210> SEQ ID NO 7
<211> LENGTH: 60
<212> TYPE: DNA
<213> ORGANISM: Artificial
<220> FEATURE:
<223> OTHER INFORMATION: Synthetic DNA

<400> SEQUENCE: 7
gatttgggat agaggagcat tagttgccat taatccaggg tgcatgctgg tacttcaaca    60

<210> SEQ ID NO 8
<211> LENGTH: 21
<212> TYPE: DNA
<213> ORGANISM: Artificial
<220> FEATURE:
<223> OTHER INFORMATION: Synthetic DNA

<400> SEQUENCE: 8
tgttgaagta ccagcatgca c                                              21

<210> SEQ ID NO 9
<211> LENGTH: 180
<212> TYPE: DNA
<213> ORGANISM: Artificial
<220> FEATURE:
<223> OTHER INFORMATION: Synthetic DNA

<400> SEQUENCE: 9
tgttgaagta ccagcatgca ccatggggga cgctgctcat cttcttaaag atttgatttt    60
tctcccataa aatgtttttt ctctttctgg taggacaaat attggcaaat tgacatgat   120 ttgggataga ggagcattag ttgccattaa tccaggtgat cgcaaatggt aagtaatttt   180

<210> SEQ ID NO 10
<211> LENGTH: 20
<212> TYPE: DNA
<213> ORGANISM: Artificial
<220> FEATURE:
<223> OTHER INFORMATION: Synthetic DNA

<400> SEQUENCE: 10
taatggcaac taatgctcct                                                20

METHOD AND REAGENT FOR GENE SEQUENCE ANALYSIS

TECHNICAL FIELD

The present invention relates to methods for nucleic acid analysis and gene nucleotide sequence analysis, and in particular, to a method for gene sequence analysis, genetic polymorphism analysis, gene mutation analysis, and gene expression analysis.

BACKGROUND ART

A method using gel electrophoresis and fluorescence detection has been widely used for DNA nucleotide sequencing. First, in this method, prepared are a large number of copies of a DNA fragment to be subjected to sequence analysis. Next, fluorescently labeled fragments having various lengths are prepared by using the 5' end of the DNA as an origin. In addition, depending on a base type of the 3' end of the DNA fragment, a fluorescent label with different wavelengths is added. The length variation having one nucleotide difference is distinguished by using gel electrophoresis. Luminescence emitted by the respective fragment groups is detected. Then, an emission wavelength color reveals the base type at the DNA terminal of the DNA fragment group under measurement. The DNA passes through a fluorescence detection unit in the order from the shortest fragment group to the longest one. Accordingly, measurement of the fluorescence color enables the terminal base type to be determined in the order from the shortest DNA. This method allows for sequencing. Such a fluorescent DNA sequencer has been widely available, and has also played a leading role in a human genome analysis. This method uses a large number of glass capillaries having an inner diameter of about 50 μm. A technique has been disclosed that uses additional terminal-detection methods, etc., and increases the number of analysis samples per analyzer (e.g., Non-Patent Literature 1).

In the meantime, a sequencing method represented by pyrosequencing which uses a stepwise chemical reaction (e.g., Patent Literature 1 and Patent Literature 2) has been receiving attention in view of handling simplicity. FIG. 13(1) shows an example illustrating the procedure. The outline is as follows. First, a primer is hybridized with a target DNA strand. Next, four types of a nucleic acid substrate for a complementary-strand synthesis (dATP, dCTP, dTTP, dGTP) are used, and the substrates are added to a reaction solution one by one in a fixed order. Then, a complementary-strand synthesis reaction is carried out. In FIG. 13(1), the nucleic acid substrate attached to the 3' end of the primer is dGTP which is complementary to nucleotide C 131 on the target. Due to the above, the other nucleic acid substrates (dATP, dCTP, dTTP) fail to cause elongation. The nucleic acid substrates which have been added to the reaction solution and have not been used for elongation are degraded by nucleases including apyrase as a representative example. Like the time of injection of dGTP shown in FIG. 13(1), when a complementary-strand synthesis reaction is carried out, a DNA complementary strand elongates, which results in production of pyrophosphate (PPi) as a byproduct. A reaction formula at this occasion is designated in FIG. 13(2). The pyrophosphate is converted to ATP by using a function of a coexisting enzyme. Then, the ATP is reacted under the presence of both luciferin and luciferase to emit luminescence (bioluminescence).

As an example, FIG. 14 illustrates luminescence during the respective substrate injections. Usually, by using this luminescence profile, the luminescence which is generated for each nucleic acid substrate added is analyzed. This analysis reveals whether or not the substrates added for the complementary-strand synthesis are incorporated into the DNA strand. Consequently, sequence information of the complementary strand, i.e., sequence information of the target DNA strand is revealed.

dATP is one type of a nucleic acid substrate for a complementary-strand synthesis, and has a structure similar to ATP which is a bioluminescence substrate. Accordingly, dATP has been known to behave as a luciferase substrate. This causes background luminescence signals, which reduce detection sensitivity. As a measure against the phenomenon, Nyren et al. use a dATP analog as a substitute for dATP, and specifically disclose use of dATPαS (Patent Literature 1).

The above-described Nyren's method has decreased background luminescence during pyrosequencing, so that the method has contributed to improvement of luminescence detection performance at the analysis. Unfortunately, the method using a nucleotide α-thiotriphosphate analog including dATPαS has disadvantages. One of the disadvantages is an enzyme activity inhibition by an Rp isomer at the phosphate group moiety. Nyren et al. disclose the above in detail (Patent Literature 3 and Non-Patent Literature 2), and specifically disclose that the Rp isomer probably inhibits a polymerase activity and that the Rp isomer cannot be degraded by apyrase. As a measure against the above, Nyren et al. disclose a technique in which only an Sp isomer is first purified and used. In addition, excessive Sp isomers are degraded into nucleotide α-thiomonophosphate analogs by apyrase. Then, a portion of the analogs is resynthesized into the nucleotide α-thiotriphosphate analogs by the enzyme. At this occasion, the probability of synthesis of the Sp/Rp isomer is each 50%, which causes a problem that the Rp isomer is synthesized and accumulated. Then, the Rp isomer is degraded and removed by alkaline phosphatase. Nyren et al. disclose that this method can circumvent the polymerase extension inhibition caused by the Rp isomer.

Further, as a nucleic acid substrate used as a substitute for dATP, Eriksson et al. disclose a method for using 7-deaza-2'-deoxyadenosine triphosphate ($C^7$dATP) (Non-Patent Literature 3). $C^7$dATP has an adenine group whose nitrogen at the 7-position is substituted by carbon. Because of this, the triphosphate structure is identical to dATP, and $C^7$dATP is easily degraded by apyrase. That is, $C^7$dATP is distinct from nucleotide α-thiotriphosphate analogs of conventional techniques. There exists no enantiomer which seems to be an inhibitory factor for the enzymes. Accordingly, Eriksson et al. disclose that nucleic acid sequence analysis can be carried out without the enzyme inhibition.

In one hand, the reaction which generates ATP from pyrophosphate uses APS. However, APS is a substrate for a luciferase reaction, and gives background luminescence. Because of this, in order to perform DNA nucleotide sequencing with high sensitivity, a method without using APS is desirable. As a feasible method to achieve this objective, a nucleotide sequencing method has been disclosed that uses a reverse reaction of an enzyme, pyruvate orthophosphate dikinase (PPDK), and utilizes a reaction of synthesizing ATP from AMP and PPi (Patent Literature 4). This method does not utilize APS which has been pointed out as a background luminescence component in conventional techniques. Therefore, this method can achieve a marked reduction in the background luminescence and has realized detection with high sensitivity.

CITATION LIST

Patent Literature

Patent Literature 1: WO98/13523
Patent Literature 2: WO98/28440
Patent Literature 3: JP Patent Publication (Kohyo) NO. 2004-508054A
Patent Literature 4: JP Patent Publication (Kokai) NO. 2007-97471A Non-Patent Literature
Non-Patent Literature 1: Anal. Chem. 72:15, 3423-3430, 2000
Non-Patent Literature 2: Anal. Biochem. 301, 82-90, 2002
Non-Patent Literature 3: Nucleosides, Nucleotides & Nucleic Acids, 23: 10, 1583-1594, 2004

SUMMARY OF INVENTION

Technical Problem

As described above, the conventional pyrosequencing methods have required use of a nucleotide α-thiotriphosphate analog substantially including dATPαS. However, the difficulty caused by using a nucleotide α-thiotriphosphate analog including dATPαS has become apparent.

One of the difficulties is, as described above, that the Rp isomer of the nucleotide α-thiotriphosphate analog inhibits a polymerase activity. Then, Nyren et al. have proposed a measure against it. In the measure, only an Sp isomer has been purified, and dATPαS (hereinafter, referred to as Sp-dATPαS) has been used.

In the meantime, the present inventors' research has demonstrated problems that: a nucleic acid elongation reaction using the Sp-dATPαS has poor efficiency of incorporation of nucleic acid substrates into the 3' end of a DNA; the nucleic acid substrates which should be usually incorporated are not incorporated; and incomplete elongation (i.e., elongation is not completed) occurs on a portion of DNA complementary-strand molecules during a complementary-strand synthesis. The occurrence of this incomplete elongation in a portion of the DNA molecules causes a decrease in analysis precision such as shortening of a nucleotide read length when an analysis object has consecutive nucleotides of T, i.e., a poly (T) region, in particular. Thus, it has been found necessary to decrease a rate of incomplete elongation.

In addition, with regard to a technique using $C^7$dATP, the present inventors' research has demonstrated that due to high similarity between $C^7$dATP and ATP, $C^7$dATP behaves as a substrate for luciferase. Because of this, application of $C^7$dATP to a pyrosequencing method has been demonstrated to markedly decrease detection sensitivity during a nucleotide elongation reaction.

Accordingly, it is an object of the present invention to provide a nucleic acid substrate which has nucleic acid substrate characteristics equivalent to those of dATP, has a low substrate specificity for luciferase, exerts no negative effect on enzymatic reactions such as a complementary-strand synthesis, and therefore is particularly suitable for the pyrosequencing method.

Solution to Problem

The present inventors have not used a dATP analog (a nucleotide α-thiotriphosphate analog including dATPαS), and have synthesized a novel substance, whose adenine group of dATP has been substituted by another purine derivative, for application. Specifically, under conditions of preserving a structure in which an amino group, contributing to a hydrogen bond, at the 6-position is attached, the substances having another purine derivative are newly synthesized. Among the substances, those which are not likely to be a substrate for luciferase and can be used for a sequence analysis have been selected. As a result, the present inventors have found that the above problems have been able to be resolved by using a 7-substituted deoxyribonucleotide triphosphate, whose 7-position of a purine group is modified by a substituent, as a complementary nucleic acid substrate for nucleotide T (thymine) in a template nucleic acid sample.

Specifically, the present invention includes the following aspects of the invention.

(1) A method for nucleic acid analysis, comprising the steps of: carrying out a complementary-strand synthesis by using a nucleic acid sample as a template and by adding complementary nucleic acid substrates for nucleotides A, G, T, and C; generating ATP from pyrophosphate generated in the complementary-strand synthesis by using an enzyme; and determining the presence or absence of the complementary-strand synthesis by detecting chemiluminescence produced in a luciferase reaction, wherein a 7-substituted deoxyribonucleotide triphosphate whose 7-position of a purine group is modified by a substituent is used as the complementary nucleic acid substrate for nucleotide T.

(2) The method for nucleic acid analysis according to (1), wherein a 7-substituted deoxyribonucleotide triphosphate whose 7-position of a purine group is modified by a substituent via an ethenyl group (a C—C double bond), an ethylene group (a C—C single bond), or an ethynyl group (a C—C triple bond) is used as the complementary nucleic acid substrate for nucleotide T.

(3) The method for nucleic acid analysis according to (2), wherein a 7-substituted deoxyribonucleotide triphosphate whose 7-position of a purine group is modified by a substituent via an ethenyl group (a C—C double bond) is used as the complementary nucleic acid substrate for nucleotide T.

(4) The method for nucleic acid analysis according to any of (1) to (3), wherein the substituent at the 7-position of the purine group is a substituent comprising an aromatic group.

(5) The method for nucleic acid analysis according to (4), wherein the aromatic group is a basic aromatic group.

(6) A complementary nucleic acid substrate reagent for nucleotide T, comprising a 7-substituted deoxyribonucleotide triphosphate whose 7-position of a purine group is modified by a substituent.

(7) The reagent according to (6), comprising a 7-substituted deoxyribonucleotide triphosphate whose 7-position of a purine group is modified by a substituent via an ethenyl group (a C—C double bond), an ethylene group (a C—C single bond), or an ethynyl group (a C—C triple bond).

(8) The reagent according to (7), comprising a 7-substituted deoxyribonucleotide triphosphate whose 7-position of a purine group is modified by a substituent via an ethenyl group (a C—C double bond).

(9) The reagent according to any of (6) to (8), wherein the substituent at the 7-position of the purine group is a substituent comprising an aromatic group.

(10) The reagent according to (9), wherein the aromatic group is a basic aromatic group.

(11) A compound selected from the following:

[Chemical Formula 1]

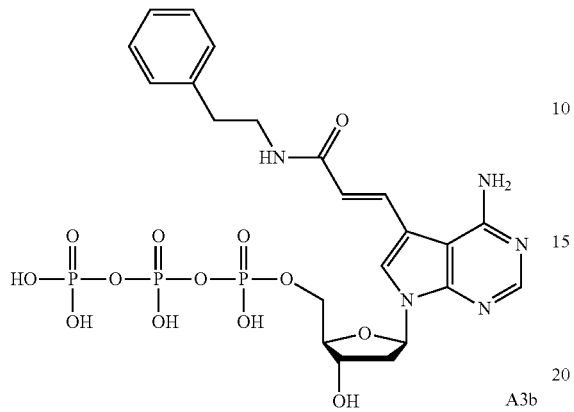

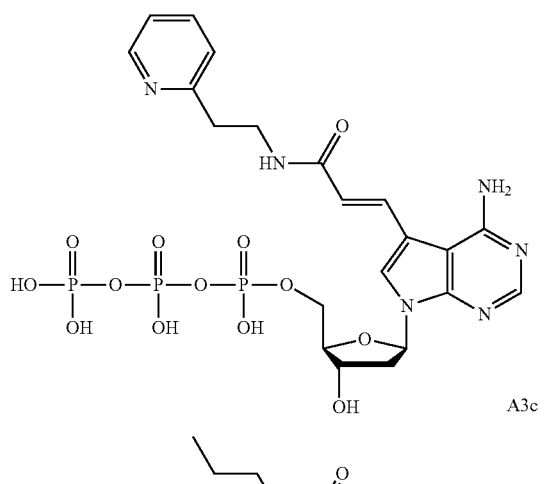

(12) A compound represented by the following formula:

[Chemical Formula 2]

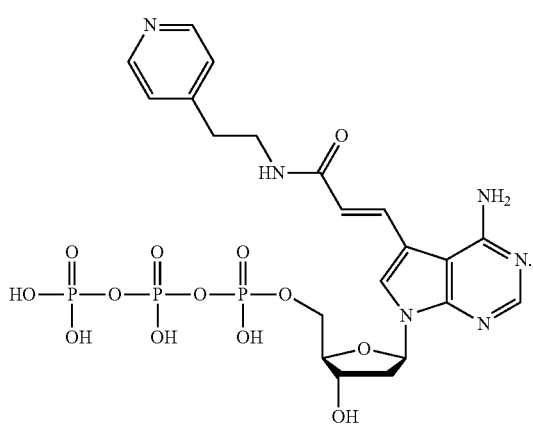

(13) The reagent according to any of (6) to (10), wherein the reagent is used for a pyrosequencing method.

The present application claims priority of Japanese Patent Application No. 2009-187917, the contents of the specification and/or Drawings of which are herein incorporated.

Advantageous Effects of Invention

The present invention does not alter a triphosphate moiety as in conventional techniques. Thus, the present invention circumvents problems that use of a dATP analog causes an insufficient complementary-strand synthesis reaction to result in the coexistence of a DNA strand having incomplete elongation, which is used to be a problem in a sequencing method using a stepwise chemical reaction. As a result, the effect of generating improper signals can be eliminated, so that the analysis precision remarkably improves. In particular, the present invention is effective in a sequence analysis of a nucleic acid sample including consecutive nucleotides of thymine.

In addition, an increase in the reaction efficiency can decrease an amount of the DNA strand having incomplete elongation. Accordingly, a sequencing method using a stepwise chemical reaction can achieve reduction of an amount of the nucleic acid substrates used, and simplification of a substrate-removal process during the respective reaction steps. Therefore, in the case of removal of the substrates by washing etc., the amount of a washing reagent should be decreased.

BRIEF DESCRIPTION OF DRAWINGS

FIG. 1 is diagrams showing 11 novel nucleic acid substrate candidates which are synthesized in Examples.

FIG. 12 is graphs showing the results of evaluating an ability of incorporation of the respective synthetic substrates into consecutive nucleotides of T.

DESCRIPTION OF EMBODIMENTS

Figure 2:
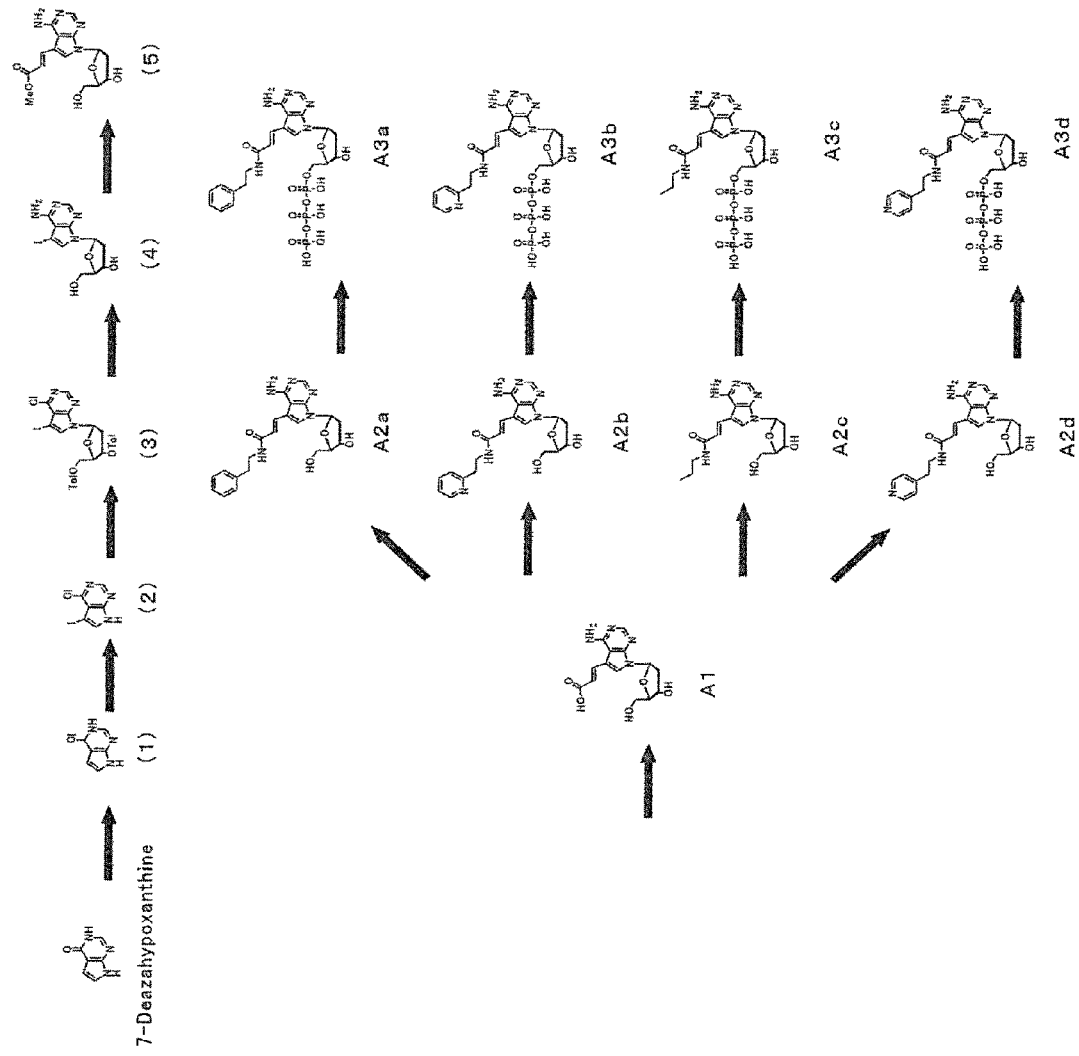
FIG. 2 is a flow chart showing a synthetic procedure for A-type nucleic acid substrates.

The present invention is characterized by a method for nucleic acid analysis, comprising the steps of: carrying out a complementary-strand synthesis by using a nucleic acid sample as a template and by adding complementary nucleic acid substrates for nucleotides A, G, T, and C; using an enzyme (e.g., ATP sulfurylase and pyruvate orthophosphate dikinase) to generate ATP from pyrophosphate generated in the complementary-strand synthesis; and determining the presence or absence of the complementary-strand synthesis by detecting chemiluminescence produced in a luciferase reaction. Preferably, the pyrosequencing method is characterized in that a 7-substituted deoxyribonucleotide triphosphate whose 7-position of a purine group is modified by a substituent is used as the complementary nucleic acid substrate for nucleotide T.

The complementary nucleic acid substrates for nucleotides A, G, T, and C refer to nucleic acid substrates which correspond to the respective nucleotides A, G, T, and C in a template, and which are incorporated into the complementary strand under synthesis during the complementary-strand synthesis from a nucleic acid sample as the template. The nucleic acid substrate includes a deoxyribonucleotide triphosphate and derivatives thereof. Usually, as a complementary nucleic acid substrate for nucleotide T, dATP (a deoxyadenosine triphosphate) and derivatives thereof can be used. As a complementary nucleic acid substrate for nucleotide A, dTTP (a thymidine triphosphate) and derivatives thereof can be used. As a complementary nucleic acid substrate for nucleotide G, dCTP (a deoxycytidine triphosphate) and derivatives thereof can be used. As a complementary nucleic acid substrate for nucleotide C, dGTP (a deoxyguanosine triphosphate) and derivatives thereof can be used. As the nucleic acid substrate, in addition to dNTPs (dATP, dGTP, dCTP, and dTTP), ddNTPs can also be used.

The present invention is characterized by using a 7-substituted deoxyribonucleotide triphosphate whose 7-position of a purine group is modified by a substituent as a complementary nucleic acid substrate for nucleotide T. The 7-substituted deoxyribonucleotide triphosphate whose 7-position of a purine group is modified by a substituent is preferably one having an amino group at the 6-position of the purine group and substituting carbon having a substituent for nitrogen at the 7-position of the purine group. Thus, it is preferable to have a structure represented by the following formula I:

[Chemical Formula 3]

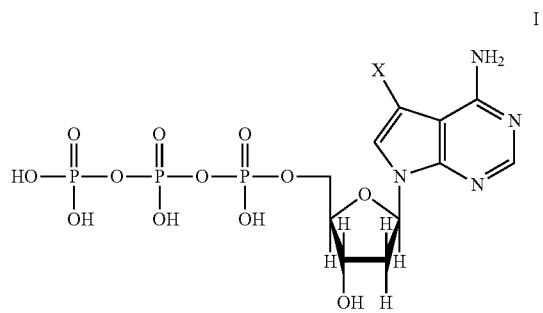

wherein the X denotes a substituent.

In addition, it is preferable to use a 7-substituted deoxyribonucleotide triphosphate whose 7-position of a purine group is modified by a substituent via an ethenyl group (a C—C double bond), an ethylene group (a C—C single bond), or an ethynyl group (a C—C triple bond) as a complementary nucleic acid substrate for nucleotide T. The above nucleic acid substrate has a lower substrate specificity for luciferase than ATP, is complementary to thymine (T) in nucleic acid, and is exclusive of guanine (G) and cytosine (C) in the nucleic acid.

The 7-substituted deoxyribonucleotide triphosphate whose 7-position of a purine group is modified by a substituent via an ethenyl group (a C—C double bond), an ethylene group (a C—C single bond), or an ethynyl group (a C—C triple bond) has a substituent at the 7-position, including, for example, substituent X in the above formula I, the substituent having a structure represented by the following respective formulae A to C:

[Chemical Formula 4]

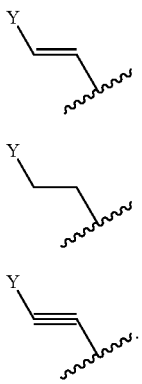

In the formulae, the wavy lines denote a site for attachment to a purine group. Y represents an organic group, and preferably represents a substituted or unsubstituted hydrocarbon group optionally having a heteroatom. Examples of the heteroatom include oxygen, nitrogen, sulfur, silicon, and phosphorus atoms. Examples of the substituent can include a halogen atom selected from fluorine, chlorine, bromine and iodine, a hydroxyl group, a substituted or unsubstituted amino, nitro, or cyano group, a substituted or unsubstituted alkyl group having 1 to 10 carbon atoms, a substituted or unsubstituted alkenyl group having 2 to 10 carbon atoms, a substituted or unsubstituted cycloalkyl group having 3 to 10 carbon atoms, a substituted or unsubstituted alkoxy group having 1 to 10 carbon atoms, and a substituted or unsubstituted alkoxycarbonyl or carboxyl group.

The 7-substituted deoxyribonucleotide triphosphate whose 7-position of a purine group is modified by a substituent, in particular, the 7-substituted deoxyribonucleotide triphosphate whose 7-position of a purine group is modified by a substituent via a ethenyl group (a C—C double bond) (i.e., one having the substituent represented by the above formula A) is particularly excellent in points that: (1) the substrate specificity for luciferase is low compared to that of ATP; (2) the 7-substituted deoxyribonucleotide triphosphate is complementary to thymine (T) in nucleic acid; (3) it is exclusive of guanine (G) and cytosine (C) in the nucleic acid; (4) it has better efficiency in its incorporation toward poly (T), consecutive nucleotides of thymine; and (5) after the incorporation, a sequencing method using a stepwise chemical reaction can be carried out as usual.

The substituent present at the 7-position of the purine group, for example, the Y in the above formulae A to C is preferably a substituent having an aromatic group. Examples of the aromatic group include a substituted or unsubstituted aromatic hydrocarbon group and a substituted or unsubstituted aromatic heterocycle group.

Examples of the aromatic hydrocarbon group include phenyl, naphthyl, phenanthryl, fluorenyl, anthryl, pyrenyl, indanyl, tetrahydronaphthyl, quinolyl, isoquinolyl, cinnolinyl, quinazolinyl, quinoxalinyl, naphthyridinyl, phthalazinyl, indolyl, isoindolyl, benzofuryl, benzothienyl, indazolyl, benzoimidazolyl, and benzothiazolyl groups.

Examples of the aromatic heterocycle group include pyridyl, pyridazinyl, pyrimidinyl, pyrazinyl, furyl, thienyl, pyrrolyl, imidazolyl, thiazolyl, and oxazolyl groups.

Examples of a substituent for the aromatic group can include a halogen atom selected from fluorine, chlorine, bromine and iodine, a hydroxyl group, a substituted or unsubstituted amino, nitro, or cyano group, a substituted or unsubstituted alkyl group having 1 to 10 carbon atoms, a substituted or unsubstituted alkenyl group having 2 to 10 carbon atoms, a substituted or unsubstituted cycloalkyl group having 3 to 10 carbon atoms, a substituted or unsubstituted alkoxy group having 1 to 10 carbon atoms, and a substituted or unsubstituted alkoxycarbonyl or carboxyl group.

The aromatic group is preferably a basic aromatic group. Examples of the basic aromatic group include pyridyl, pyrrolyl, imidazolyl, bipyridyl, pyrazinyl, pyrimidinyl, pyridazinyl, indolizinyl, indolyl, indazolyl, quinonyl, purinyl, and acridinyl, phenanthrolinyl groups. The basic aromatic group is preferably a pyridyl group, in particular, a 4-pyridyl group.

In the above formulae A to C, the Y preferably has a structure represented by the following formula II or III:

[Chemical Formula 5]

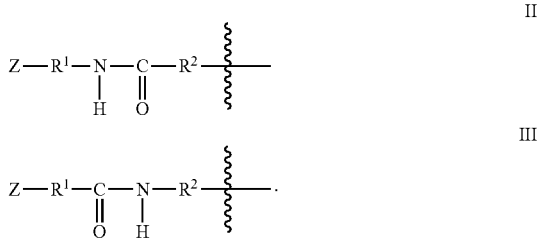

In the formulae, the wavy lines denote a site for attachment to a substituent, i.e., a site for attachment to an ethenyl group (a C—C double bond), an ethylene group (a C—C single bond) or an ethynyl group (a C—C triple bond). $R^1$ and $R^2$ are each independently a divalent organic group or a direct bond. The Z represents an organic group.

Examples of the divalent organic group preferably include a substituted or unsubstituted divalent hydrocarbon group optionally having a heteroatom. Examples of the divalent hydrocarbon group include a saturated or unsaturated aliphatic hydrocarbon group having the number of chain members of 1 to 20, preferably chain members of 1 to 10, and more preferably chain members of 1 to 6, such as an alkylene group having the number of chain members of 2 to 20, preferably chain members of 2 to 10, and more preferably chain members of 2 to 6, an alkenylene group having the number of chain members of 2 to 20, preferably chain members of 2 to 10, and more preferably chain members of 2 to 6, an alkynylene group having the number of chain members of 2 to 20, preferably chain members of 2 to 10, and more preferably chain members of 2 to 6, and a divalent alicyclic hydrocarbon group having the number of chain members of 3 to 20, preferably chain members of 3 to 10, and more preferably chain members of 3 to 6. In the above hydrocarbon group, a portion of the carbon may be substituted by a heteroatom. Examples of the heteroatom group include oxygen, nitrogen, sulfur, silicon, and phosphorus atoms.

As used herein, examples of the substituent can include a halogen atom selected from fluorine, chlorine, bromine and iodine, a hydroxyl group, a substituted or unsubstituted amino, nitro, or cyano group, a substituted or unsubstituted alkyl group having 1 to 10 carbon atoms, a substituted or unsubstituted alkenyl group having 2 to 10 carbon atoms, a substituted or unsubstituted cycloalkyl group having 3 to 10 carbon atoms, a substituted or unsubstituted alkoxy group having 1 to 10 carbon atoms, and a substituted or unsubstituted alkoxycarbonyl or carboxyl group.

Examples of the organic group Z can include an aromatic group, a halogen atom selected from fluorine, chlorine, bromine, and iodine, a hydroxyl group, substituted or unsubstituted amino (e.g., —NH—CO—CF$_3$, —NH—C(NH)—NH$_2$), nitro, or cyano group, a substituted or unsubstituted alkyl group having 1 to 10 carbon atoms, a substituted or unsubstituted alkenyl group having 2 to 10 carbon atoms, a substituted or unsubstituted cycloalkyl group having 3 to 10 carbon atoms, a substituted or unsubstituted alkoxy group having 1 to 10 carbon atoms, and a substituted or unsubstituted alkoxycarbonyl or carboxyl group. The organic group Z is preferably an aromatic group, more preferably a basic aromatic group, and still more preferably a pyridyl group.

Specifically, the below-selected 7-substituted deoxyribonucleotide triphosphate is preferable, A3a to A3d are more preferable, and the 7-substituted deoxyribonucleotide triphosphate represented by A3d is still more preferable. The 7-substituted deoxyribonucleotide triphosphate represented by A3a to A3d, in particular, by A3d is excellent in points that: (1) the substrate specificity for luciferase is 1/1000 or less than that of ATP; (2) the 7-substituted deoxyribonucleotide triphosphate is complementary to thymine (T) in nucleic acid; (3) it is exclusive of guanine (G) and cytosine (C) in the nucleic acid; (4) it has better efficiency in its incorporation toward poly (T), consecutive nucleotides of thymine; and (5) after the incorporation, a sequencing method using a stepwise chemical reaction can be carried out as usual.

[Chemical Formula 6]

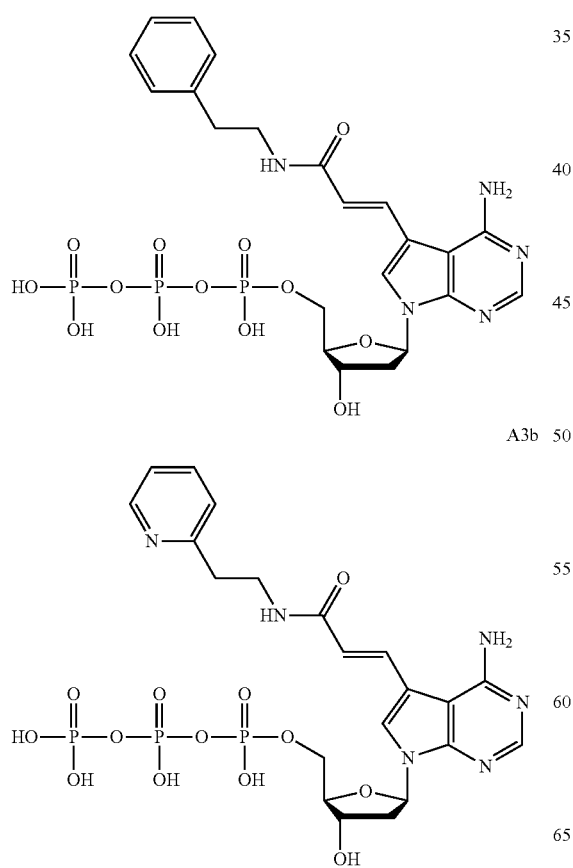

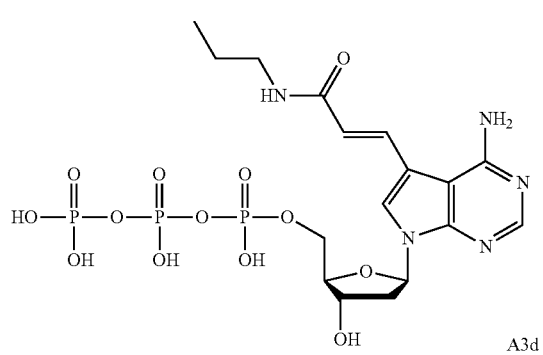

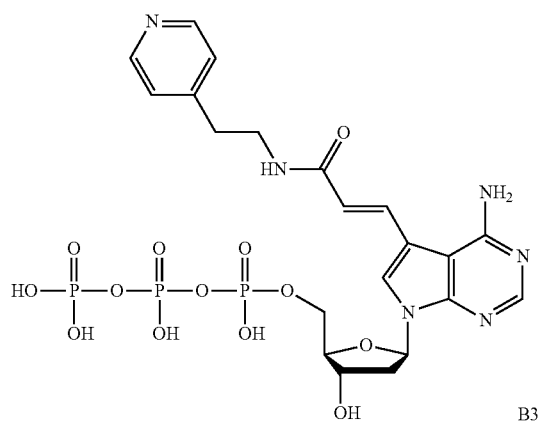

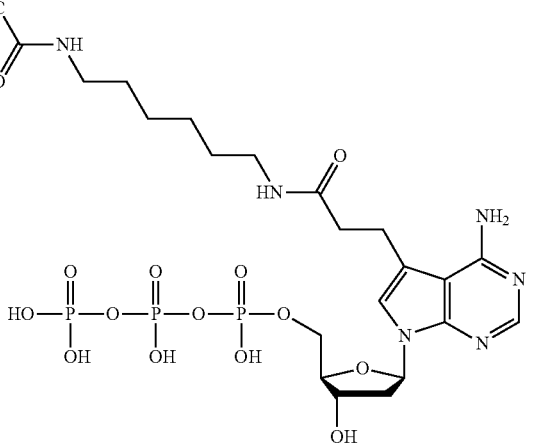

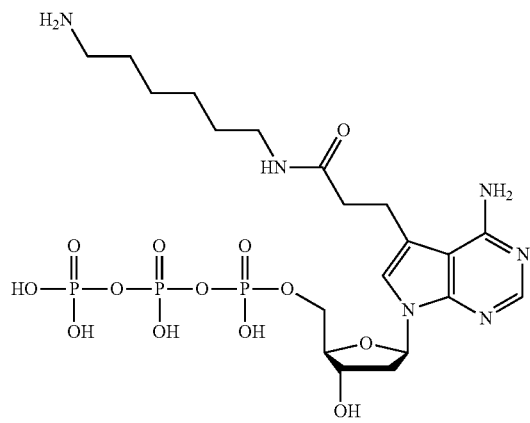

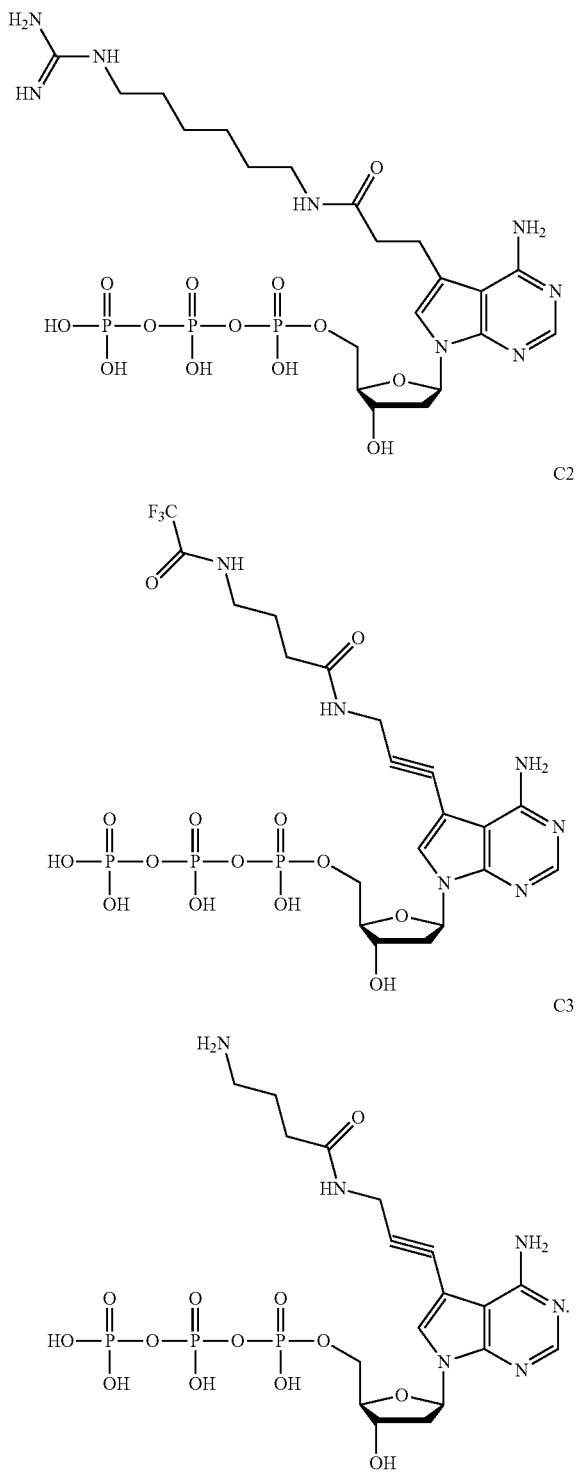

A method for nucleic acid analysis using the above nucleic acid substrates according to the present invention is a method for nucleic acid analysis, comprising the steps of: carrying out a complementary-strand synthesis by using a nucleic acid sample as a template and by adding complementary nucleic acid substrates for nucleotides A, G, T, and C; using an enzyme to generate ATP from pyrophosphate generated in the complementary-strand synthesis; and determining the presence or absence of the complementary-strand synthesis by detecting chemiluminescence produced in a luciferase reaction. The method for nucleic acid analysis is preferably a pyrosequencing method.

The method for nucleic acid analysis according to the present invention detects, via chemiluminescence produced in a luciferase reaction, pyrophosphate (PPi) generated in a primer elongation reaction of a complementary strand binding to a template nucleic acid sample. This chemiluminescence reaction catalyzed by luciferase has been known as a method for rapidly detecting ATP with high sensitivity. The reaction is also referred to as a luciferin-luciferase reaction, which depends on ATP. The luciferin is reacted with ATP to yield adenylate luciferin. This adenylate luciferin and an enzyme are decomposed under the presence of luciferase by oxidative decarboxylation. Then, a portion of energy obtained during this reaction process is liberated as a reaction called luminescence. Quantification of this luminescence enables ATP to be quantified.

Pyrophosphate (PPi) produced as a result of the complementary-strand synthesis is converted to ATP by an ATP-generating enzyme. Coexistence of luciferase, which catalyzes a chemiluminescence reaction by using ATP as a substrate, allows for detection of chemiluminescence depending on ATP generated.

ATP sulfurylase, pyruvate orthophosphate dikinase (PPDK) or phenylalanine racemase can be used for an ATP-generating enzyme which generates ATP from pyrophosphate. In addition, either DNA or RNA may be used as a nucleic acid sample. With regard to DNA, both a single strand and a double strand can be analyzed. When the double strand DNA is a template, a method of an embodiment of the present invention can be carried out after a pretreatment step of denaturing the double strand into single strands. In addition, with regard to RNA, products as obtained after reverse transcription can be analyzed by a method of an embodiment of the present invention. When a trace amount of DNA is used, an extension product which has been amplified by a PCR reaction (an amplified nucleic acid fragment) can be used. When a trace amount of mRNA is used, a reaction product according to a PCR-based oligo (G)-tailing method (Y. Y. Kusov et al., Nucleic Acids Res, 29, e57 (2001)) can be used. Hereinafter, a procedure of a method for nucleic acid analysis according to an embodiment of the present invention is described as an example.

First, a primer is hybridized with a nucleic acid sample of measurement subject. Next, a complementary-strand synthesis reaction (usually, a complementary-strand synthesis reaction by using a DNA polymerase) is carried out. At this occasion, as a nucleic acid substrate reagent, deoxyribonucleotide triphosphate (or derivatives thereof) solutions are each added sequentially. Then, only when a complementary-strand synthesis reaction occurs, PPi is produced. The produced PPi is converted into ATP under the presence of APS (adenosine 5'-phosphosulfate) by using ATP sulfurylase, or under the presence of AMP (5'-adenylate) and PEP by using pyruvate orthophosphate dikinase (PPDK). The converted ATP is used for an oxidation reaction of luciferin by using luciferase under the presence of a magnesium ion and $O_2$ (oxygen), which results in light emission. The nucleic acid substrate reagents are sequentially added and this process is repeated. Accordingly, a nucleotide sequence can be determined one by one in respect to a base type while detecting the presence or absence of luminescence (see, Ahmadian A et al., Analytical Biochemistry 280 (2000) 103-110 and Zhou G et al., Electrophoresis 22 (2001) 3497-3504). It is preferable to add a nucleic acid substrate reagent at a final concentration of 1 to 10 µM, and preferably 2 to 4 µM.

Excessive nucleic acid substrates or derivatives thereof after the complementary-strand synthesis reaction become an undesirable factor for measurement, so that these substrates are preferably rapidly removed by enzyme-mediated degradation, etc. Examples of the enzyme used can include apyrase, and pyrophosphatase (PPase). In addition, the Klenow fragment, in which an exonuclease activity is removed, is preferable for a DNA polymerase used in the complementary-strand synthesis. From a viewpoint of the enzyme activity and complementary-strand synthesis reaction, the reaction solution is preferably adjusted to have a pH of 7.0 to 8.0 and a temperature of 30 to 45° C. Further, a trace amount of an enzyme such as pyrophosphatase is preferably added beforehand to the reagent to decompose and remove PPi and ATP, which cause background, from the reagent.

Hereinafter, the present invention will be described with reference to Examples. However, the present invention is not limited to these Examples.

EXAMPLES

Example 1

Synthesis of Novel Nucleic Acid Substrates

First, dATP of a nucleic acid substrate has a purine group, whose 6-position has an amino group, at 1'-position of a ribose of a nucleotide triphosphate. The purine group whose 6-position has an amino group is referred to as an adenine group. Selective base-pairing exerted complementarily between an adenine group and a thymine group is due to hydrogen bonds involved with nitrogen at the 1-position and the amino group at the 6-position of the purine group. Because of this, as a substrate candidate which is available for nucleic acid elongation, it seemed to be critical under conditions absolutely having an amino group at the 6-position to modify another position. Furthermore, since the 1-position and the 6-position of the purine group contribute to binding to a complementary strand, modifications were planned to be made at positions far from the above positions. Then, a plurality of types of a deoxyribonucleotide triphosphate whose 7-position or 8-position of the purine group was modified were synthesized as follows. Hereinafter, the synthetic procedure is described.

At this time, the present inventors synthesized 11 novel nucleic acid substrate candidates illustrated in FIG. 1, and assessed their properties. The respective 11 species can be classified as below. Four species of A3a to A3d (hereinafter, referred to as A-type compounds) are a series in which the 7-position of the purine group is modified by a substituent via an ethenyl group (a C—C double bond). Three species of B3 to B5 (hereinafter, referred to as B-type compounds) is a series in which the 7-position of the purine group is modified by a substituent via an ethylene group (a C—C single bond). C2 and C3 (hereinafter, referred to as C-type compounds) is a series in which the 7-position of the purine group is modified by a substituent via an ethynyl group (a C—C triple bond). D2 and D3 (hereinafter, referred to as D-type compounds) is a series in which the 8-position of the purine group is modified by a substituent via an ethynyl group (a C—C triple bond). Synthetic procedures of the respective substances are described below.

FIG. 2 shows a synthetic procedure for A-type compounds (in a flow chart). The synthetic procedure for A-type compounds is as follows.

<Synthesis of A1>

$PoCl_3$ (10 mL, 0.11 mol, F.W. 153.3, 15 eq.) was added to vacuum-dried 7-deazahypoxanthine (1.00 g, $7.4 \times 10^{-3}$ mol, F.W. 135.13), and the mixture was heated under reflux for 45 minutes in an oil bath at 115° C. After the reaction had been completed, the mixture was distilled away under reduced pressure, and a small amount of cold water was added to a residue and the reaction was quenched. Then, that solution was dissolved in diethyl ether and was washed with distilled water. After an organic phase was dried over anhydrous magnesium sulfate, suction filtration was carried out, and a filtrate was distilled away under reduced pressure to yield target substance 1.

The vacuum-dried target substance 1 (1.03 g, 6.92 mmol, F.W. 153.57) was added to dry-DMF (38 mL) and suspended. Next, a dry-DMF solution containing N-iodosuccinimide (1.71 g, 7.62 mmol, 1.1 eq.) (30 mL) was added, and the mixture was stirred under an argon atmosphere for 3 hours at room temperature. After the reaction solution was distilled away under reduced pressure, a residue was dissolved in ethyl acetate (70 mL), and was washed twice with saturated aqueous sodium bicarbonate (30 mL). After an organic phase was dried over anhydrous magnesium sulfate, suction filtration was carried out, and a filtrate was distilled away under reduced pressure. A residue was dissolved in ethyl acetate (10 mL), and dichloromethane was added to recrystallize. The recrystallized product was subjected to suction filtration to yield target substance 2. A filtrate was purified by silica gel column chromatography (silica gel 60, 40 to 50 µm, 0 to 3% methanol/ethyl acetate) to yield the target substance 2.

The vacuum-dried target substance 2 (1.932 g, 6.97 mmol, F.W. 279.47) was suspended in dry-acetonitrile (100 mL), and sodium hydride (60% in oil, 7.61 mmol, 1.1 eq.) was added thereto under an argon atmosphere. Next, the mixture was stirred at room temperature for 30 minutes. Then, 1-(α)-chloro-3,5-di-O-(p-toluoyl)-2-deoxy-D-ribose (3.76 g, 9.69 mmol, 1.4 eq.) was slowly added over 20 minutes, and the mixture was stirred at room temperature for 2 hours. The reaction solution was distilled away under reduced pressure, and a residue was dissolved in dichloromethane (200 mL) and washed with aqueous sodium bicarbonate. After an organic phase was dried over anhydrous magnesium sulfate, filtration was carried out, and a filtrate was distilled away under reduced pressure. The resulting substance was purified by silica gel column chromatography (silica gel 60, 40 to 50 µm, 25% methanol/ethyl acetate) to yield target substance 3.

The target substance 3 (500 mg, 0.791 mmol, F.W. 631.85) was suspended in a saturated ammonium ethanol solution. Next, the mixture was stirred in a pressure-resistant vessel at 65° C. for 20 hours, and the reaction solution was distilled away under reduced pressure. A residue was dissolved in methanol (30 mL), and saturated aqueous ammonia (30 mL) was added thereto. The mixture was stirred for 5 hours, and the reaction solution was distilled away under reduced pressure. Then, a residue was dissolved in a small amount of methanol, and was recrystallized with hexane. The recrystallized product was subjected to suction filtration to yield target substance 4.

The vacuum-dried target substance 4 (300 mg, 0.780 mmol, F.W. 376.15) was dissolved in dry-pyridine (5 mL), and azeotropy was carried out three times and the mixture was vacuum-dried overnight. After the atmosphere was substituted with argon, the vacuum-dried mixture was dissolved in dry-DMF (6 mL) and degassing was performed. Methyl acrylate (30 mL, 0.33 mmol, F.W. 86.09, 420 eq.), copper iodide (CuI, 41 mg, 0.215 mmol, 0.2 eq.), triphenylphosphine palladium ($Pd(PPh_3)_4$, 125 mg, 0.108 mmol, 0.1 eq.), triethylamine (0.3 mL, 2.15 mmol, 2 eq.) was sequentially added thereto, and the mixture was stirred at 65° C. for 7 hours. The reaction solution was distilled away under reduced pressure, and was purified by silica gel column chromatography (silica gel 60, 40 to 50 μm, 0 to 5% methanol/ethyl acetate) to yield oily target substance 5.

The target substance 5 (35 mg, 104 μmol, F.W. 334.33) was dissolved in 1 N NaOHaq (4 ml), and the mixture was stirred overnight at room temperature. The reaction solution was neutralized with 4 N HClaq, and a precipitated crystal was subjected to suction filtration to yield target substance A1.

<Synthesis of A3a>

The vacuum-dried target substance A1 (140 mg, 437 μmol, F.W. 320.30), for which an atmosphere was substituted with argon, Py BOP (273 mg, 524 μmol, 1.2 eq), and HOBt.H$_2$O (80 mg, 524 μmol, 1.2 eq) were dissolved in DMF (1 ml), and DIPEA (761 μl, 4.37 mmol, 10 eq) and 2-phenylethylamine (110 μl, 1.04 mmol, 2.0 eq) were further added thereto and the mixture was stirred at room temperature for 3 hours. The reaction solution was distilled away under reduced pressure, and was purified by silica gel chromatography. Then, purification was carried out again by using a medium-pressure reverse-phase column to yield target substance A2a.

After nucleoside A2a (109 mg, 257 μmol, F.W. 423.47) was converted into an azeotrope with DMF (2 ml), N,N,N',N'-tetramethyl-1,8-naphthalenediamine (ProtonSponge, 82 mg, 385 μmol, 1.5 eq) was added thereto and the mixture was dried overnight. After trimethyl phosphate (1.5 ml) was added to the resulting mixture to dissolve therein, the mixture was cooled to 0° C. Phosphonyl chloride (38 μl, 411 μmol, 1.6 eq) was added dropwise, and the mixture was stirred at 0° C. for 45 minutes. An additional DMF solution (2.57 mL, 1.28 mmol, 5.0 eq) containing tributylamine (245 μl, 1.01 mmol, 4.0 eq) and 0.5 M tributylammonium pyrophosphate was added at 0° C., and thereafter, the temperature of the reaction solution was returned to room temperature to carry out a reaction for 1 hour. The reaction was terminated by adding 1.0 M aqueous triethylammonium bicarbonate (pH 8.0, 4 mL) and water (4 mL). Then, the reaction solution was distilled away under reduced pressure. Subsequently, a residue was dissolved in water and washed twice with diethyl ether, and an aqueous phase was eluted by using a DEAE-Sephadex A-25 column and a buffer with a salt gradient (0.3 to 1.0 M) having aqueous triethylammonium bicarbonate (pH 8.0). This effluent was purified by using a medium-pressure column to yield target substance A3a.

<Synthesis of A3b>

The vacuum-dried A1 (120 mg, 374 μmol, F.W. 320.30), for which an atmosphere was substituted with argon, Py BOP (234 mg, 449 μmol, 1.2 eq), HOBt.H$_2$O (68 mg, 449 μmol, 1.2 eq) were dissolved in DMF (650 μl), and DIPEA (650 μl, 3.74 mmol, 10 eq) and 2-(2-aminoethyl)pyridine (89 μl, 748 μmol, 2.0 eq) were further added thereto and the mixture was stirred at room temperature for 3 hours. The reaction solution was distilled away under reduced pressure, and was purified by silica gel chromatography. Then, purification was carried out again by using a medium-pressure reverse-phase column to yield target substance A2b.

After nucleoside A2b (100 mg, 235 μmol F.W. 424.45) was converted into an azeotrope with DMF (2 ml), N,N,N',N'-tetramethyl-1,8-naphthalenediamine (ProtonSponge, 75 mg, 352 μmol, 1.5 eq) was added thereto and the mixture was dried overnight. After trimethyl phosphate (1.5 ml) was added to the resulting mixture to dissolve therein, the mixture was cooled to 0° C. Phosphonyl chloride (35 μl, 376 μmol, 1.6 eq) was added dropwise, and the mixture was stirred at 0° C. for 45 minutes. An additional DMF solution (2.40 mL, 1.17 mmol, 5.0 eq) containing tributylamine (225 μl, 940 μmol, 4.0 eq) and 0.5 M tributylammonium pyrophosphate was added at 0° C., and thereafter, the temperature of the reaction solution was returned to room temperature to carry out a reaction for 1 hour. The reaction was terminated by adding 1.0 M aqueous triethylammonium bicarbonate (pH 8.0, 4 mL) and water (4 mL). Then, the reaction solution was distilled away under reduced pressure. Subsequently, a residue was dissolved in water and washed twice with diethyl ether, and an aqueous phase was eluted by using a DEAE-Sephadex A-25 column and a buffer with a salt gradient (0.3 to 1.0 M) having aqueous triethylammonium bicarbonate (pH 8.0). This effluent was purified by using a medium-pressure column to yield target substance A3b.

<Synthesis of A3c>

The vacuum-dried A1 (150 mg, 468 μmol, F.W. 320.30), for which an atmosphere was substituted with argon, Py BOP (292 mg, 561 μmol, 1.2 eq), HOBt.H$_2$O (86 mg, 561 μmol, 1.2 eq) was dissolved in DMF (817 μl), and DIPEA (817 μl, 4.68 mmol, 10 eq) and n-propylamine (76 μl, 963 μmol, 2.0 eq) were further added thereto and the mixture was stirred at room temperature for 3 hours. The reaction solution was distilled away under reduced pressure, and was purified by silica gel chromatography. Then, purification was carried out again by using a medium-pressure reverse-phase column to yield target substance A2c.

After nucleoside A2c (109 mg, 301 μmol, F.W. 361.40) was converted into an azeotrope with DMF (2 ml), N,N,N',N'-tetramethyl-1,8-naphthalenediamine (ProtonSponge, 97 mg, 451 μmol, 1.5 eq) was added thereto and the mixture was dried overnight. After trimethyl phosphate (1.5 ml) was added to the resulting mixture to dissolve therein, the mixture was cooled to 0° C. Phosphonyl chloride (45 μl, 481 μmol, 1.6 eq) was added dropwise, and the mixture was stirred at 0° C. for 45 minutes. An additional DMF solution (3.0 mL, 1.50 mmol, 5.0 eq) containing tributylamine (288 μl, 1.20 mmol, 4.0 eq) and 0.5 M tributylammonium pyrophosphate was added at 0° C., and thereafter, the temperature of the reaction solution was returned to room temperature to carry out a reaction for 1 hour. The reaction was terminated by adding 1.0 M aqueous triethylammonium bicarbonate (pH 8.0, 4 mL) and water (4 mL). Then, the reaction solution was distilled away under reduced pressure. Subsequently, a residue was dissolved in water and washed twice with diethyl ether, and an aqueous phase was eluted by using a DEAE-Sephadex A-25 column and a buffer with a salt gradient (0.3 to 1.0 M) having aqueous triethylammonium bicarbonate (pH 8.0). This effluent was purified by using a medium-pressure column to yield target substance A3c.

<Synthesis of A3d>

Nucleoside A1 (140 mg, 0.44 mmol, F.W. 320), Py BOP (274 mg, 0.53 mmol, F.W. 520, 1.2 eq.), and HOBt (82 mg, 0.53 mmol, F.W. 153, 1.2 eq.) were blended together, and the mixture was vacuum-dried overnight. The mixture was dissolved in a small amount of DMF, and DIEPA (500 μL, 2.95 mmol, 6.7 eq.) was added and the mixture was stirred for 10 seconds. Then, 4-(2-aminoethyl)pyridine (105 μL, 0.89 mmol, F.W. 122, 1.83 eq.) was rapidly added, and the resulting mixture was stirred at room temperature for 1 hour. After the reaction, the reaction solution was distilled away under reduced pressure, and a residue was dissolved in methanol and purified by using a medium-pressure column to yield target substance A2d.

Azeotropy of nucleoside A2d (85 mg, 0.20 mmol, F.W. 424) with DMF (6 mL) was carried out twice, and azeotropy with acetonitrile (3 mL) was carried out three times. After the nucleoside A2d was vacuum-dried for 3 hours, N,N,N',N'- tetramethyl-1,8-naphthalenediamine (ProtonSponge, 65 mg, 0.30 mmol, 1.5 eq.) was added thereto and the mixture was dried overnight. After trimethyl phosphate (1.5 ml) was added under an argon atmosphere to the resulting mixture to dissolve therein, the mixture was cooled to 0° C. Phosphonyl chloride (30 μL, 0.32 mmol, 1.6 eq.) was added dropwise, and the mixture was stirred at 0° C. for 45 minutes. An additional DMF solution (2.1 mL, 1.05 mmol, 5 eq.) containing tributylamine (0.19 mL, 0.79 mmol, 4.0 eq.) and 0.5 M tributylammonium pyrophosphate was added at 0° C., and thereafter, the temperature of the reaction solution was returned to room temperature to carry out a reaction for 1 hour. The reaction was terminated by adding 1.0 M aqueous triethylammonium bicarbonate (pH 8.0, 4 mL) and water (4 mL). Then, the reaction solution was distilled away under reduced pressure. Subsequently, a residue was dissolved in water and washed twice with diethyl ether, and an aqueous phase was eluted by using a DEAE-Sephadex A-25 column and a buffer with a salt gradient (0.3 to 1.0 M) having aqueous triethylammonium bicarbonate (pH 8.0). This effluent was purified by using a medium-pressure column to yield target substance A3d.

<Synthesis of B-Type Compounds>

Figure 3:
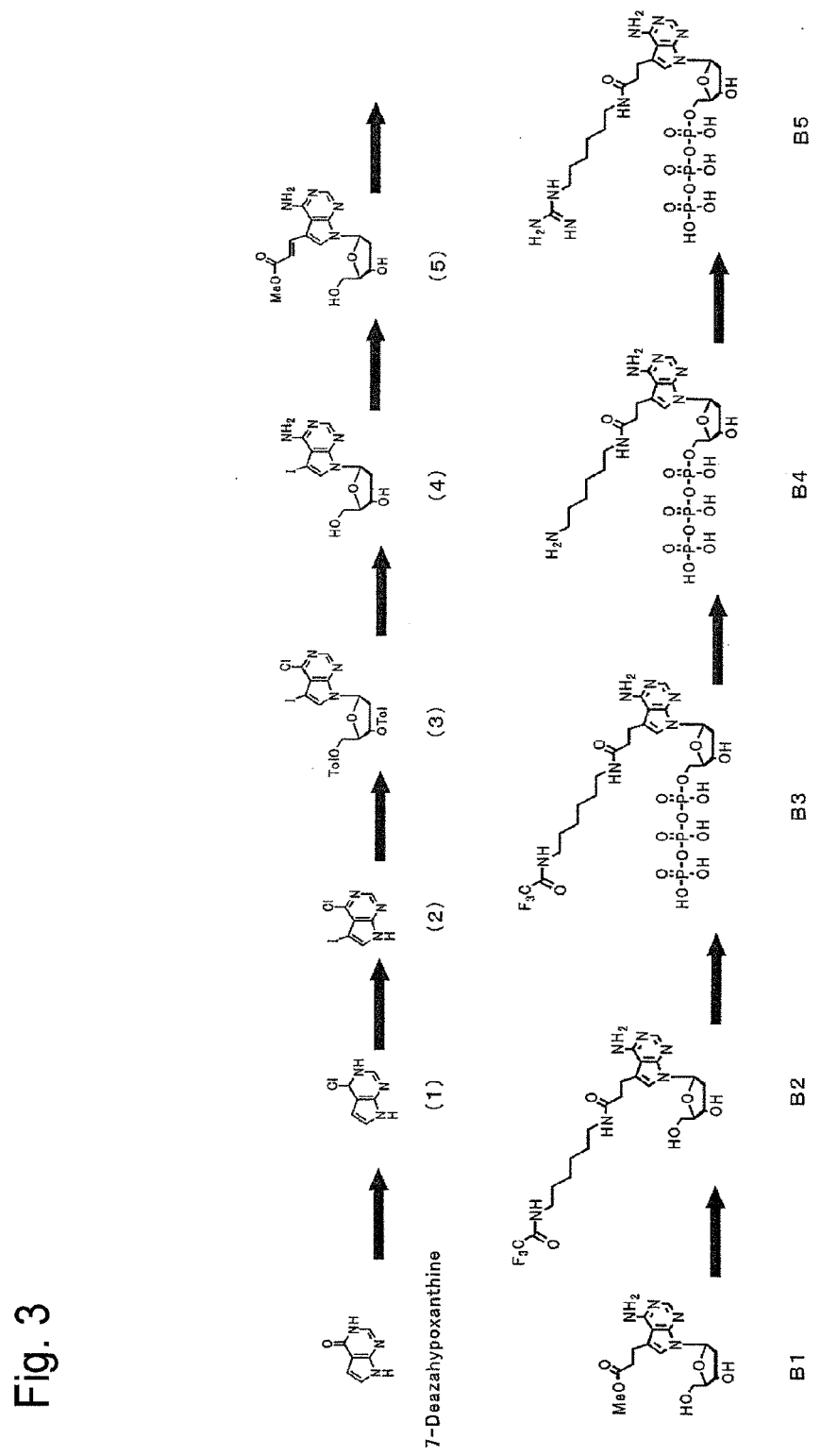
FIG. 3 is a flow chart showing a synthetic procedure for B-type nucleic acid substrates.

Next, FIG. 3 shows a synthetic procedure for B-type compounds (in a flow chart). The synthetic procedure for B-type compounds is as follows. It is notable that up to the synthesis of target substance 5, the procedure is the same as in the previous description.

The vacuum-dried target substance 5 (262 mg, 0.78 mmol, F.W. 336) was dissolved in dry-methanol (30 mL). Next, platinum oxide (IV) (10 mg, 0.044 mmol, F.W. 227.08) was added. Then, $H_2$ was injected into a balloon and the mixture was stirred at room temperature for 2 hours while blowing. The reaction solution was subjected to natural filtration, and a filtrate was distilled away under reduced pressure. After that, the filtrate was purified by silica gel column chromatography (silica gel 60, 40 to 50 μm, 10% methanol/dichloromethane) to yield target substance B1.

Nucleoside B1 (36 mg, 0.11 mmol, F.W. 336.33) and DMAP (1.31 mg, 0.011 mmol, F.W. 122.17, 0.1 eq.) were vacuum-dried overnight. Then, a dry-methanol solution (0.8 mL) containing 1,6-diaminohexane (125 mg, 1.1 mmol, 10 eq.) was added, and the mixture was heated under reflux at 52° C. for 24 hours. Since the reaction had been completed, the reaction solution was distilled away under reduced pressure. Next, in order to remove a large amount of 1,6-diaminohexane as much as possible, reprecipitation was carried out. A residue was dissolved in methanol (1 mL), and was added dropwise to diethyl ether (45 mL) under ice-cooling while stirring to precipitate the residue. This precipitate was subjected to suction filtration to yield 70 mg of light brown powder containing a target substance. This powder containing a crude product (70 mg, 0.17 mmol, F.W. 420.51) was dissolved in methanol (1.4 mL). Then, triethylamine (0.092 mL, 0.68 mmol, 4 eq.) and ethyl trifluoroacetate (0.2 mL, 1.7 mmol, 10 eq.) were added, and the mixture was stirred at room temperature for 13.5 hours. Since the reaction had not been completed, ethyl trifluoroacetate (0.2 mL, 1.7 mmol, 10 eq.) was further added and the mixture was stirred at room temperature for 1 hour. The reaction solution was distilled away under reduced pressure, was purified by silica gel column chromatography (silica gel 60, 40 to 50 μm, 3 to 12% methanol/chloroform) to yield light brown powder containing target substance B2.

Azeotropy of nucleoside B2 (106 mg, 0.21 mmol, F.W. 516.51) with DMF (6 mL) was carried out twice, and azeotropy with acetonitrile (3 mL) was carried out three times. After the nucleoside B2 was vacuum-dried for 3 hours, N,N,N',N'-tetramethyl-1,8-naphthalenediamine (ProtonSponge, 66 mg, 0.31 mmol, 1.5 eq.) was added thereto and the mixture was dried overnight. After trimethyl phosphate (1.47 ml) was added under an argon atmosphere to the resulting mixture to dissolve therein, the mixture was cooled to 0° C. Phosphonyl chloride (31 μl, 0.33 mmol, 1.6 eq.) was added dropwise, and the mixture was stirred at 0° C. for 45 minutes. An additional DMF solution (2.12 mL, 1.0 mmol, 5 eq.) containing tributylamine (0.20 mL, 0.82 mmol, 4.0 eq.) and 0.5 M tributylammonium pyrophosphate was added at 0° C., and thereafter, the temperature of the reaction solution was returned to room temperature to carry out a reaction for 1 hour. The reaction was terminated by adding 1.0 M aqueous triethylammonium bicarbonate (pH 8.0, 4 mL) and water (4 mL). Then, the reaction solution was distilled away under reduced pressure. Subsequently, a residue was dissolved in water and washed twice with diethyl ether, and an aqueous phase was eluted by using a DEAE-Sephadex A-25 column and a buffer with a salt gradient (0.3 to 1.0 M) having aqueous triethylammonium bicarbonate (pH 8.0). This effluent was purified by using a medium-pressure column to yield target substance B3.

First, 4 N aqueous ammonia (5 mL) was added to nucleotide B3 (830 μL, 74.6 at OD260 nm, $5.0 \times 10^{-6}$ mol, F.W. 756.44), and the mixture was stirred at room temperature for 2 hours. After the reaction had been completed, the reaction solution was distilled away under reduced pressure, and a residue was purified by using a medium-pressure column to yield target substance B4.

Then, 1.0 M TB1/DMF (513 μL, 0.513 mmol, 220 eq.) was added to lyophilized B4 (35 at OD260 nm, 440 μmol, F.W. 660.45), and the mixture was dissolved. TEA (0.143 mL, 1.03 mmol, 440 eq.) was further added, and the resulting mixture was stirred at room temperature for 7 hours. After the reaction had been completed, the reaction solution was distilled away under reduced pressure, and a residue was purified by high performance liquid chromatography to yield target substance B5.

<Synthesis of C-Type Compounds>

Figure 4:
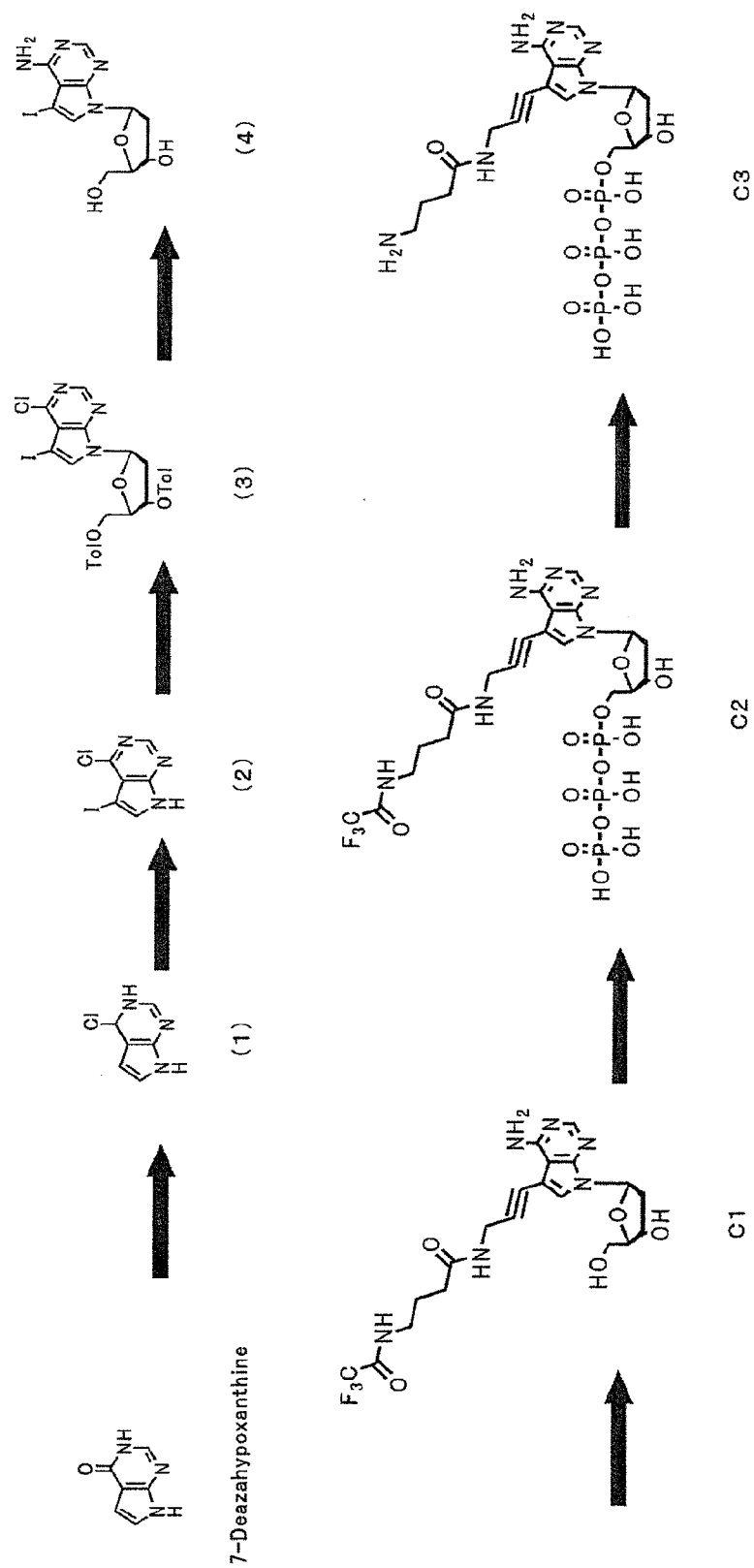
FIG. 4 is a flow chart showing a synthetic procedure for C-type nucleic acid substrates.

Next, FIG. 4 shows a synthetic procedure for C-type compounds (in a flow chart). The synthetic procedure for C-type compounds is as follows. It is notable that up to the synthesis of target substance 4, the procedure is the same as in the previous description.

The vacuum-dried target substance 4 (100 mg, 0.27 mmol, F.W. 376.15) and TN2 (314 mg, 1.33 mmol, 5 eq.) were dissolved in dry-DMF (4 mL), and the mixture was freezed using liquid nitrogen. Then, degassing was carried out four times by using an oil pump. Copper iodide (CuI, 64 mg, 0.37 mmol, 1.26 eq.), triphenylphosphine palladium ($Pd(PPh_3)_4$, 62 mg, 0.053 mmol, 0.2 eq.), triethylamine (0.074 mL, 2 equivalent) were sequentially added thereto, and the mixture was stirred at 35° C. for 7 hours. The reaction solution was distilled away under reduced pressure, purified by silica gel column chromatography (silica gel 60, 40 to 50 μm, 3 to 10% methanol/dichloromethane), and distilled away under reduced pressure. A residue was purified by using a medium-pressure column. Desalting was carried out using a reverse-phase column to yield target substance C1.

Azeotropy of nucleoside C1 (95 mg, 0.20 mmol, F.W. 484.4) with DMF (6 mL) was carried out twice, and azeotropy with acetonitrile (3 mL) was carried out three times. After the nucleoside C1 was vacuum-dried for 3 hours, N,N,N',N'-tetramethyl-1,8-naphthalenediamine (ProtonSponge, 63.3 mg, 0.30 mmol, 1.5 eq.) was added thereto and the mixture was dried overnight. After trimethyl phosphate (1.5 ml) was added under an argon atmosphere to the resulting mixture to dissolve therein, the mixture was cooled to 0° C. Phosphonyl chloride (29.3 μL, 0.32 mmol, 1.6 eq.) was added dropwise, and the mixture was stirred at 0° C. for 45 minutes. An additional DMF solution (1.97 mL, 0.99 mmol, 5 eq.) containing tributylamine (0.19 mL, 0.79 mmol, 4.0 eq.) and 0.5 M tributylammonium pyrophosphate was added at 0° C., and thereafter, the temperature of the reaction solution was returned to room temperature to carry out a reaction for 1 hour. The reaction was terminated by adding 1.0 M aqueous triethylammonium bicarbonate (pH 8.0, 4 mL) and water (4 mL). Then, the reaction solution was distilled away under reduced pressure. Subsequently, a residue was dissolved in water and washed twice with diethyl ether, and an aqueous phase was eluted by using a DEAE-Sephadex A-25 column and a buffer with a salt gradient (0.3 to 1.0 M) having aqueous triethylammonium bicarbonate (pH 8.0). This effluent was purified by using a medium-pressure column to yield target substance C2.

Then, 4 N aqueous ammonia (5 mL) was added to nucleotide C2 (700 μL, 70 at OD260 nm, $4.6 \times 10^{-6}$ mol, F.W. 725.44), and the mixture was stirred at room temperature for 2 hours. After the reaction had been completed, the reaction solution was distilled away under reduced pressure and the residue was purified by high performance liquid chromatography to yield target substance C3.

<Synthesis of D-Type Compounds>

Figure 5:
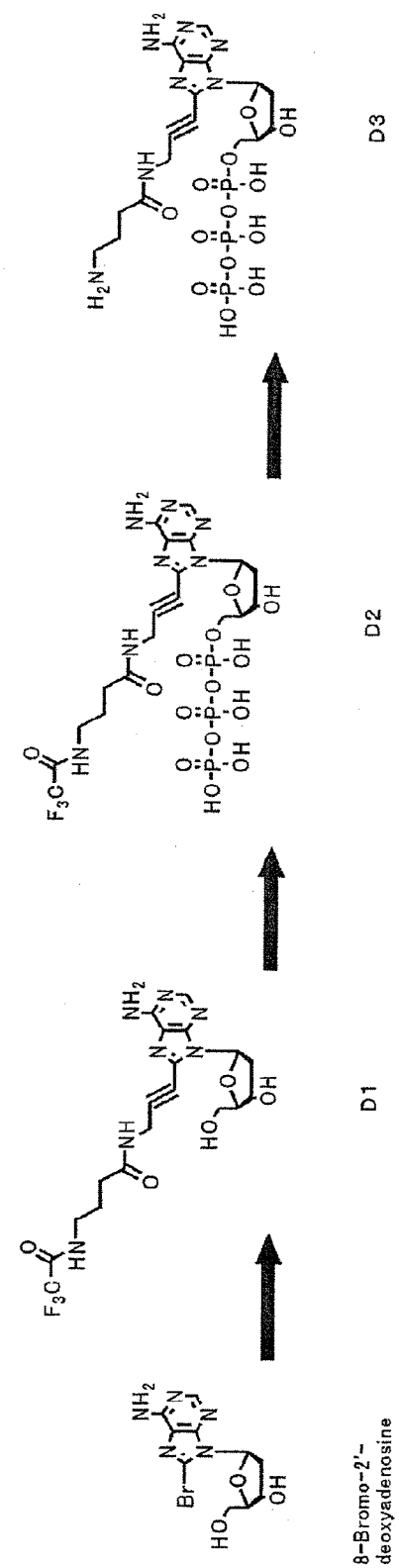
FIG. 5 is a flow chart showing a synthetic procedure for D-type nucleic acid substrates.

Finally, FIG. 5 shows a synthetic procedure for D-type compounds (in a flow chart). The synthetic procedure for D-type compounds is as follows.

Vacuum-dried 8-bromo-2'-deoxyadenosine (100 mg, 0.30 mmol, F.W. 330.14) and TN2 (357 mg, 1.5 mmol, 5 eq.) were dissolved in dry-DMF (4 mL), and the mixture was freezed using liquid nitrogen. Then, degassing was carried out four times by using an oil pump. Copper iodide (CuI, 72.6 mg, 0.38 mmol, 1.26 eq.), triphenylphosphine palladium (Pd(PPh$_3$)$_4$, 70 mg, 0.06 mmol, 0.2 eq.), triethylamine (0.05 mL, 2 eq.) were sequentially added thereto, and the mixture was stirred at 35° C. for 7 hours. The reaction solution was distilled away under reduced pressure, purified by silica gel column chromatography (silica gel 60, 40 to 50 μm, 3 to 10% methanol/dichloromethane), and distilled away under reduced pressure. A residue was purified by using a medium-pressure column. Desalting was carried out using a reverse-phase column to yield target substance D1.

Azeotropy of nucleoside D1 (78 mg, 0.16 mmol, F.W. 485.4) with DMF (6 mL) was carried out twice, and azeotropy with acetonitrile (3 mL) was carried out three times. After the nucleoside D1 was vacuum-dried for 3 hours, N,N,N',N'-tetramethyl-1,8-naphthalenediamine (ProtonSponge, 51.8 mg, 0.24 mmol, 1.5 eq.) was added thereto and the mixture was dried overnight. After trimethyl phosphate (1.16 ml) was added under an argon atmosphere to the resulting mixture to dissolve therein, the mixture was cooled to 0° C. Phosphonyl chloride (37.4 μL, 0.40 mmol, 1.6 eq.) was added dropwise, and the mixture was stirred at 0° C. for 45 minutes. An additional DMF solution (1.61 mL, 0.81 mmol, 5 eq.) containing tributylamine (0.16 mL, 0.64 mmol, 4.0 eq.) and 0.5 M tributylammonium pyrophosphate was added at 0° C., and thereafter, the temperature of the reaction solution was returned to room temperature to carry out a reaction for 1 hour. The reaction was terminated by adding 1.0 M aqueous triethylammonium bicarbonate (pH 8.0, 4 mL) and water (4 mL). Then, the reaction solution was distilled away under reduced pressure. Subsequently, a residue was dissolved in water and washed twice with diethyl ether, and an aqueous phase was eluted by using a DEAE-Sephadex A-25 column and a buffer with a salt gradient (0.3 to 1.0 M) having aqueous triethylammonium bicarbonate (pH 8.0). This effluent was purified by using a medium-pressure column to yield target substance D2.

Then, 4 N aqueous ammonia (5 mL) was added to nucleotide D2 (100 μL, 10 at OD260 nm, $1.7 \times 10^{-6}$ mol, F.W. 725.44), and the mixture was stirred at room temperature for 2 hours. After the reaction had been completed, the reaction solution was distilled away under reduced pressure and the residue was purified by high performance liquid chromatography to yield target substance D3.

Example 2

Evaluation of Substrate Specificity for Luciferase

In respect to the nucleic acid substrates synthesized, whether or not the substrates became a substrate for luciferase was evaluated by the following procedure. First, a luminescence reagent designated in Condition 1 of Table 1 was prepared.

TABLE 1

Luminescence Reagent Composition

| Composition | Luminescence Reagent Condition 1 | Luminescence Reagent Condition 2 | Luminescence Reagent Condition 3 |
|---|---|---|---|
| Tricine | 25 mM | 25 mM | 25 mM |
| EDTA | 0.5 mM | 0.5 mM | 0.5 mM |
| Mg-Acetate | 5 mM | 5 mM | 5 mM |
| DTT | 0.5 mM | 0.5 mM | 0.5 mM |
| ATP sulfurylase | 2 U/mL | 2 U/mL | 2 U/mL |
| Luciferase | 262 GLU/mL | 131 GLU/mL | 131 GLU/mL |
| Luciferin | 0.4 mM | 0.4 mM | 0.4 mM |
| APS | 0.002 mM | 0.002 mM | 0.002 mM |
| Apyrase | 1 U/mL | 1 U/mL | 1.5 U/mL |

Figure 6:
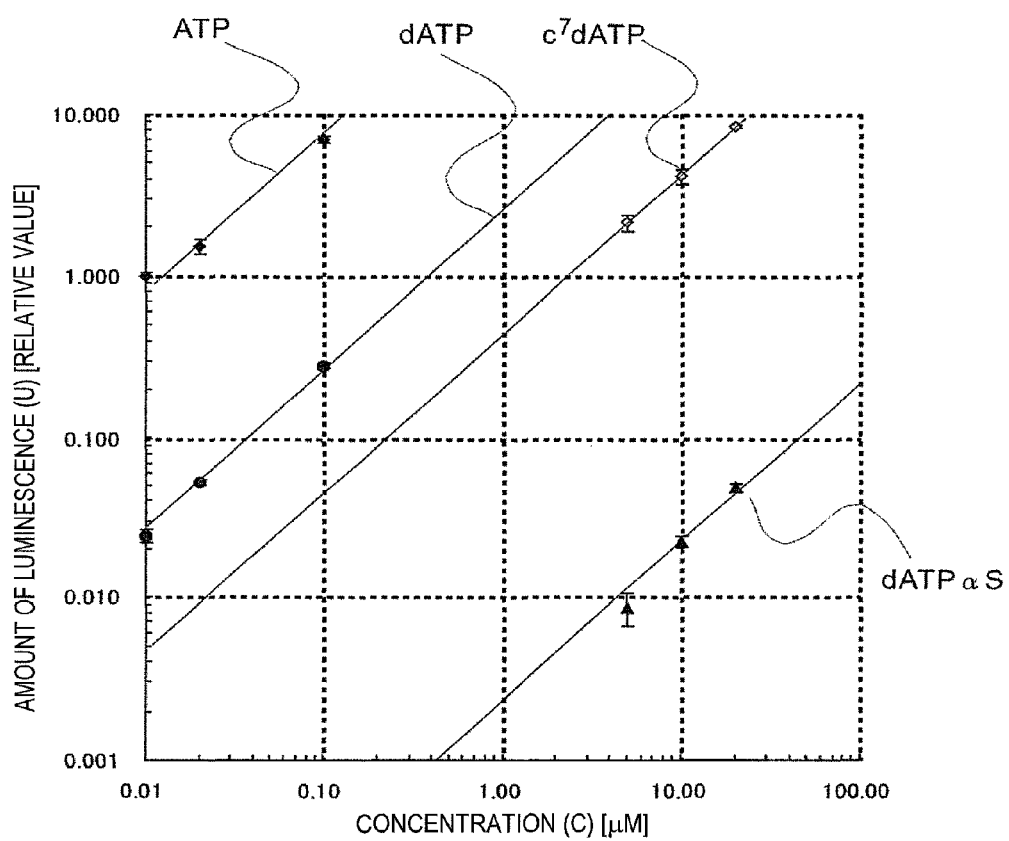
FIG. 6 is a graph showing the amount of luminescence when ATP, dATP, and dATPαS are each dispensed as a substrate.

Next, a reaction solution was prepared using 20 μL of this luminescence reagent, and 0.2 μL of a nucleic acid substrate of evaluation subject was injected. Then, luminescence emitted at this occasion was estimated. FIG. 6 is a graph showing the amount of luminescence when ATP, dATP, C$^7$dATP, and dATPαS are each dispensed as a substrate. The abscissa (C) indicates a final concentration of the compound in a reaction reagent. For example, when 0.2 μl of 1 μM substrate is dispensed, the final concentration is about 0.01 μM. An amount of luminescence (U) indicated in the ordinate was plotted by normalizing the amount of luminescence at 0.01 μM of ATP as 1. From this graph, the amount of luminescence (U) is found to be proportional to the final concentration (C). Because of this, as a substrate specificity (or substrate reactivity) for luciferase, the value (S) indicating the amount of luminescence per unit concentration is defined as described below.

Substrate specificity $(S)$=Amount of luminescence $(U)$/Final concentration $(C)$[μM]×0.01

(In this Definition, the Substrate Specificity of ATP is Normalized as 1).

Figure 7:
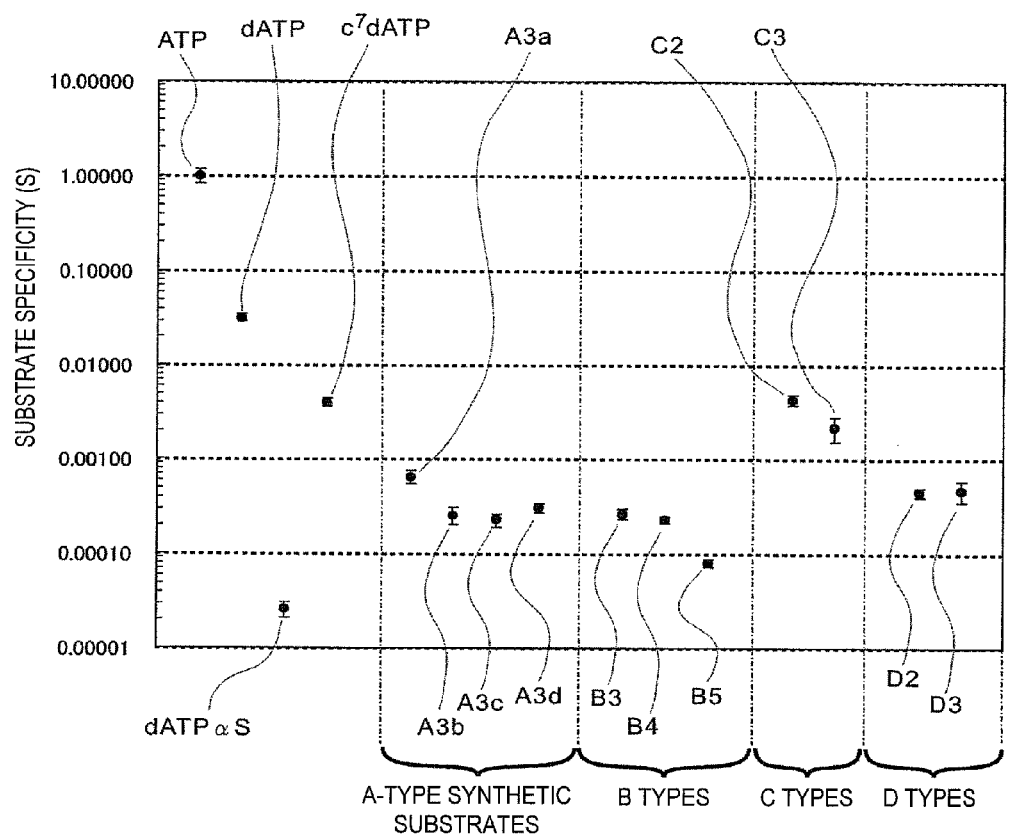
FIG. 7 is a graph showing the results of measuring a substrate specificity for luciferase in respect to nucleic acid substrates synthesized.

With regard to the nucleic acid substrates synthesized, FIG. 7 showed the results of measuring a substrate specificity for luciferase according to the above-described procedure. The four points designated in the left side of the graph indicate each substrate specificity (S) of ATP, dATP, dATPαS, and C$^7$dATP. For a sequencing method using a stepwise chemical reaction represented by pyrosequencing, the amount of ATP generated from pyrophosphate produced in elongation of one nucleotide is equivalent to the amount of a target present in a reaction solution when all of the targets have been elongated. In addition, elongation of a plurality of nucleotides causes the amount to be multiplied by the number of the nucleotides. Generally speaking, the amount of a nucleic acid substrate which should be dispensed per reaction for sequencing requires about 100 times the amount of the target for analysis. This is because a sequenced region may sometimes contain about 10 consecutive identical nucleotides; and a reaction solution for this sequencing method has a substrate-degrading enzyme together, so that the nucleic acid elongation and substrate degradation are competed. Shortage of the substrates causes incomplete elongation, so that the following sequence analysis cannot be carried out. This results in occurrence of increased analysis errors and incapability. As a countermeasure against it, the substrate having about 100 times the target amount which has been generally used is preferably dispensed per reaction.

In view of the above, in order to definitely measure the amount of luminescence caused by ATP generated during elongation of one nucleotide, it is ideal that the substrate specificity (S) of the nucleic acid substrate dispensed is 1/1000 or less of that of ATP. Among conventionally used pseudo-nucleic acid substrates, dATPαS has an excellent substrate specificity that is 1/10000 or less of that of ATP. In contrast, the substrate specificity of $C^7$dATP is about 1/250 of that of ATP.

Thus, this specificity does not meet the ideal condition of 1/1000 or less. Due to the above, $C^7$dATP-derived background luminescence can be predicted to exert influence on sequence analysis precision.

Next, the results of evaluating the nucleic acid substrates synthesized in this Example are described. First, FIG. 7 indicates that in order to decrease a substrate specificity for luciferase, it is preferable to use an ethenyl group (a C—C double bond) or an ethylene group (a C—C single bond) as a modified group.

In this Example, the synthesized nucleic acid substrates were purified by liquid chromatography. However, removal of pyrophosphate that had been incorporated during the synthesis may be insufficiently carried out only by liquid chromatography-mediated purification. At that occasion, the present inventors treated the synthesized nucleic acid substrates by a pyrophosphate-degrading enzyme (PPase) to decompose the pyrophosphate. Specifically, the synthesized nucleic acid substrate was diluted in a reaction solution (100 mM Tris-Acetate, 0.5 mM EDTA, 5 mM Mg-Acetate, 1 mM DTT, pH 7.5) at a concentration of 500 µM. Then, PPase was added at 0.2 mU/µL, and the mixture was reacted at 30° C. for 30 minutes, which caused degradation of pyrophosphate in the solution. This method represents one example. However, this method completely degrades pyrophosphate in the nucleic acid substrate, and is thus effective in evaluations of the correct substrate specificity (S) and sequencing with high accuracy. In addition, with regard to ATP, dATP, dATPαS, and $C^7$dATP which had been used for comparative experiments, removal of pyrophosphate contained was carried out in a similar manner for evaluation.

Example 3

Evaluation of Ability of Incorporation into Nucleic Acid

A nucleic acid substrate as a substitute for dATP should satisfy the following prerequisite.

(1) The nucleic acid substrate can complementarily bind to nucleotide T (it has an affinity).

(2) The nucleic acid substrate is exclusive of nucleotide G, nucleotide C, or nucleotide A.

(3) In the case of consecutive nucleotide T, the nucleic acid substrate is continuously incorporated.

These conditions were verified as described below. The following is sequences of the oligo DNA used for evaluation. The left terminal of the sequences indicates the 5' end, and the right terminal indicates the 3' end.

```
Sequence TG (SEQ ID NO: 1):
gactgaat ataaacttgt ggtagttgga gctgttggcg taggcaagag tgccttgacgatacagctaa ttc Sequence GA (SEQ ID NO: 2):
gactgaat ataaacttgt ggtagttgga gctagtggcg taggcaagag tgccttgacgatacagctaa ttc Sequence CG (SEQ ID NO: 3):
gactgaat ataaacttgt ggtagttgga gctgctggcg taggcaagag tgccttgacgatacagctaa ttc Sequence AG (SEQ ID NO: 4):
gactgaat ataaacttgt ggtagttgga gctgatggcg taggcaagag tgccttgacgatacagctaa ttc Sequence 5T (SEQ ID NO: 5):
acgttttttggcg taggcaagag tgcctt Sequence P (SEQ ID NO: 6):
aaggc actct tgcct acgcc a
```

Of note is that Sequence P represents a primer sequence. This primer can complementarily bind to the underlined portion of the above sequences. Other portions of the sequences represent template sequences corresponding to a nucleotide which is incorporated when the primer complementarily binds to the portions and the 3' end of the primer is elongated. For example, Sequence TG indicates template nucleotides at the site of elongation of the 3' end of the primer, which means that the sequence of the primer binding portion is next to T and G in the direction toward its 5' end. In addition, Sequence 5T means that the sequence of the primer binding portion is next to 5 consecutive T in the direction toward its 5' end in a similar manner.

Incorporation into nucleic acid was evaluated as follows. First, one of the above sequences was used as a target. Next, the primer was made to complementarily bind to the target. Then, an elongation experiment was carried out using the respective nucleic acid substrates for that sample. The synthesized nucleic acid substrate requires an affinity (complementary characteristics) with nucleotide T, and exclusivity of the other nucleotides (G, C, and A). The affinity with nucleotide T was evaluated using the Sequence TG and the primer. The exclusivity of the other nucleotides (G, C, and A) was evaluated using the respective Sequence GA, Sequence CG, and Sequence AG, and the primer. In addition, Sequence 5T was used for the evaluation of an ability of continuous incorporation into nucleotide T.

A sequencing method using a stepwise chemical reaction is described below. First, 35 µL of ultrapure water, 5 µL of oligo DNA (10 µM) of analysis object (target), and 5 µL of a primer (20 µM) were mixed with 5 µL of a hybridization buffer (10 mM Tris-Acetate, 20 mM Mg-Acetate, pH 7.75) (a sample solution: the final volume was 50 µL). Then, the sample solution was heated at 94° C. for 20 seconds, and reacted at a Tm temperature of the primer for 2 minutes. After that, 0.5 µL, (target: 0.5 µmol, primer: 1 µmol) of this sample solution, 20 of a luminescence reagent which is designated in Condition 2 of Table 1, and 0.2 µL of a polymerase enzyme (the final concentration: 0.05 U/4) were mixed to prepare a reaction reagent (the final volume was 20.7 µL). To this reaction reagent was added 0.4 µL of 100 µM nucleic acid substrate (the final concentration 2 µM). When nucleic acid elongation occurs, bioluminescence derived from pyrophosphate of the elongation reaction product can be observed. That reaction is carried out according to a chemical reaction formula shown in FIG. 13(2). The reaction has a luminescence peak a few seconds after the reaction initiation. Then, a luminescence profile exhibits an asymptotic decay curve. This luminescence peak value is virtually proportional to the amount of generated pyrophosphate. Measurement of the peak value enables a degree of nucleic acid elongation to be estimated.

Figure 8:
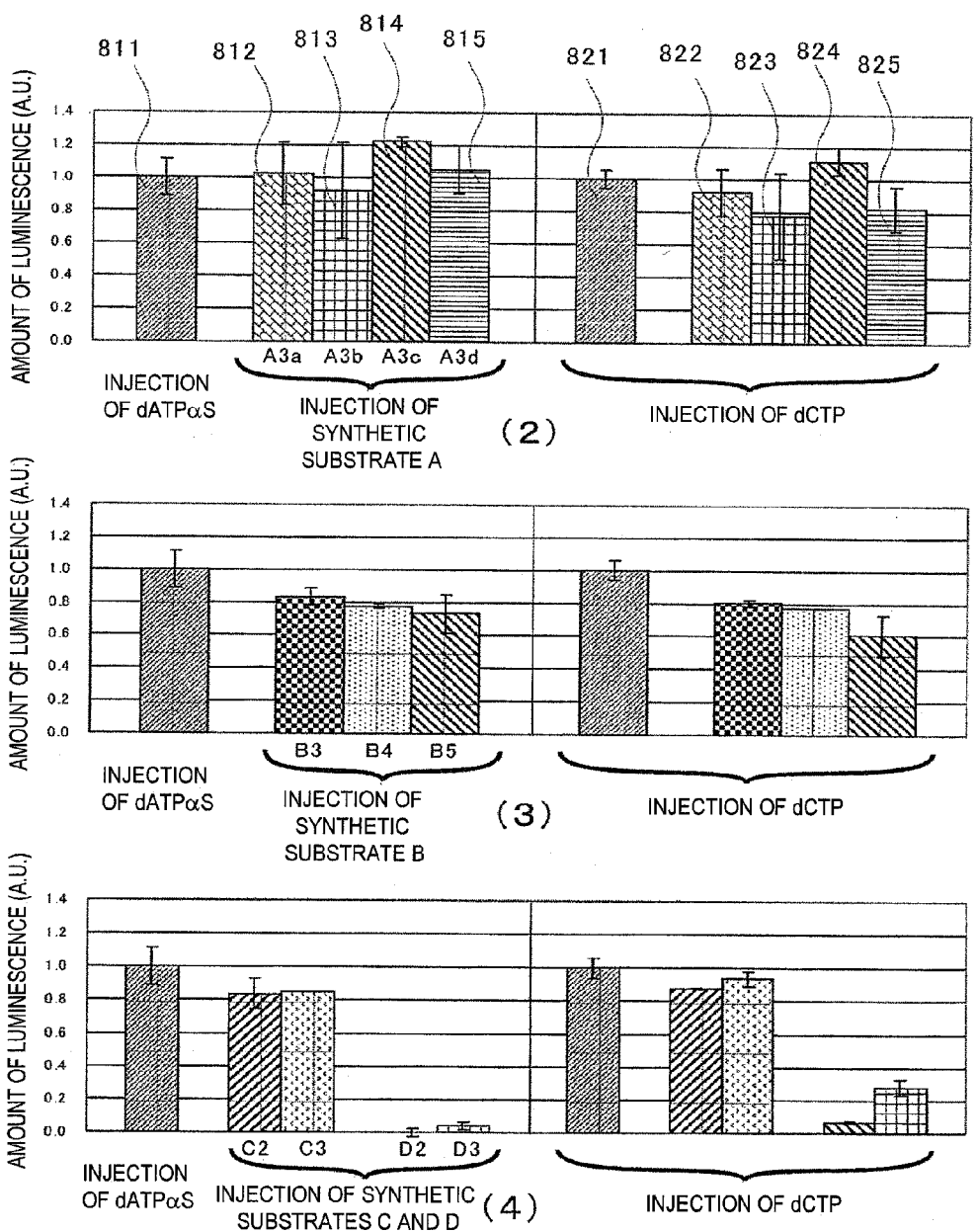
FIG. 8 is graphs showing the results of evaluating an affinity between synthetic substrates and nucleotide T.

FIG. 8 shows the results of evaluating an affinity between synthetic substrates and nucleotide T by using Sequence TG as a target. A target 81 and a primer 82 form a complementary strand binding as illustrated in FIG. 8(1). A synthetic substrate added is linked and elongated to a nucleotide A 83 that is the 3' end nucleotide of the primer when the substrate complementarily binds to a nucleotide T 84. Pyrophosphate generated by the elongation is converted to ATP by using a chemical reaction designated in FIG. 13(2) to induce luciferase-mediated luminescence. In this experiment, dCTP was dispensed afterward. This is because after the 3' end of the primer becomes the synthetic substrate due to the elongation reaction, dCTP that is a substrate complementary to an adjacent nucleotide G 85 is dispensed to verify whether or not substrate incorporation of the substrate into the end having the synthetic substrate is carried out normally. FIGS. 8(2) to (4) show the results of evaluating the amount of luminescence regarding luciferase-mediated luminescence. The left portion indicates an amount of luminescence at the time of dispensing the respective synthetic substrates. The right portion indicates an amount of luminescence at the time of dispensing dCTP afterward. Of note is that the amount of luminescence was expressed by normalizing amounts of luminescence 811 and 821, which consisted one nucleotide equivalent in the case of using dATPαS of a conventional technique, as 1. In addition, a background luminescence component of the respective substrates was compensated by taking its difference into account. The luminescence of A3a, A3b, A3c, and A3d in the case of using each synthetic nucleotide is 812, 813, 814, and 815, respectively. In addition, the amounts of luminescence at the time of subsequently dispensing dCTP into these samples are 822, 823, 824, and 825, respectively.

Figure 9:
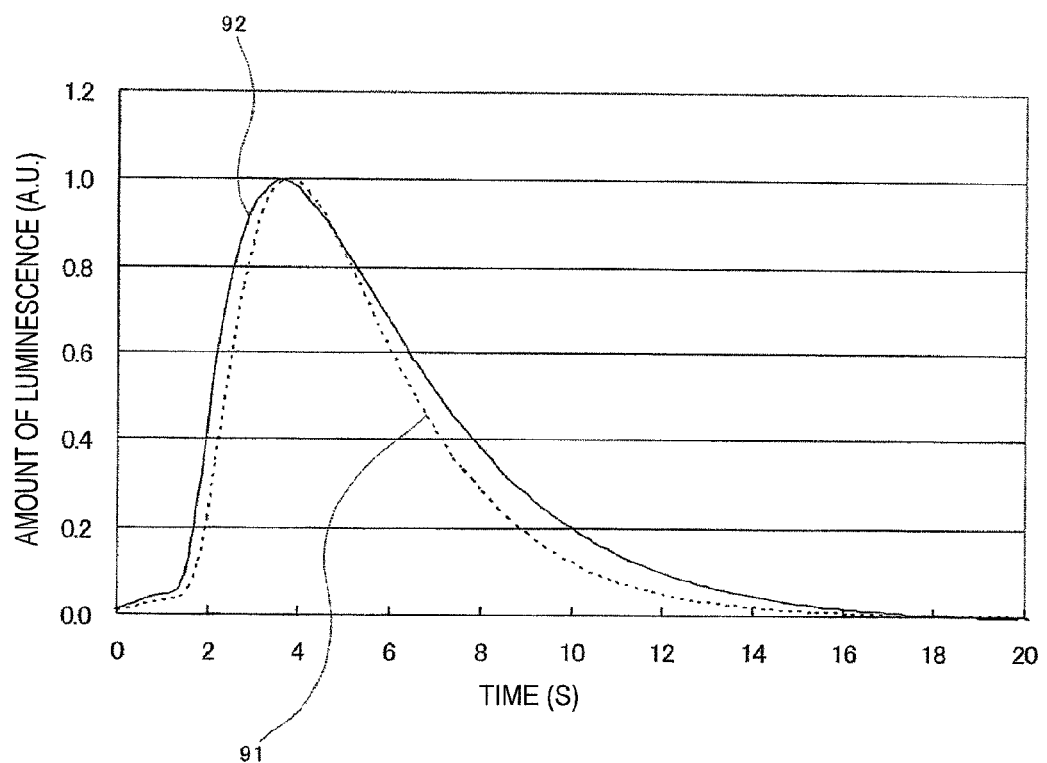
FIG. 9 is a graph showing a comparison of the luminescence profile between dATPαS and A3c.

This result has lead to the following. First, FIG. 8(2) demonstrated that four synthetic substrates of A type were able to be used as substrates complementary to nucleotide T in a manner similar to the case of using dATPαS of a conventional technique. Among them, the substrate A3c was distinct from other substrates, and exhibited an about 10 to 20% higher amount of luminescence. This is because the substrate A3c possesses a higher rate of a nucleic acid elongation reaction than other substrates. In FIG. 9, luminescence profiles between dATPαS and A3c are compared. The broken line 91 denotes a profile of dATPαS. The solid line 92 denotes a profile of A3c. For comparison, the maximum values of both the profiles are normalized as 1, and are depicted. This graph demonstrates that A3c exhibits a steeper rise curve, and thus has a higher reaction rate. This reaction is a competitive reaction between luminescence derived from pyrophosphate supplied by nucleic acid elongation and quenching due to substrate degradation by apyrase, a degrading enzyme. As a rise rate increases, the luminescence rises more rapidly while competing with the apyrase-mediated degradation. Consequently, the maximum value of the luminescence becomes higher. As a result, A3c seems to exhibit about 10 to 20% higher amount of luminescence than other substrates.

Next, FIG. 8(3) demonstrated that B-type substrates were able to be used as substrates complementary to nucleotide T in a manner similar to A-type compounds, but exhibited a relatively slower reaction rate. In addition, FIG. 8(4) verified that C-type substrates were able to be used as substrates complementary to nucleotide T in a similar fashion. Last, D-type substrates were found to be unable to elongate. It remains elusive that the D-type substrates were unable to act as a substrate complementary to nucleotide T or they had a reduced ability to attach to the 3' end. In either case, it was found impossible to use them as a substrate complementary to nucleotide T. The D-type substrates are a synthetic substrate whose 8-position of the purine has been modified, so that the 8-position-modified compounds are found to be unsuitable for an object of the present invention.

Figure 10:
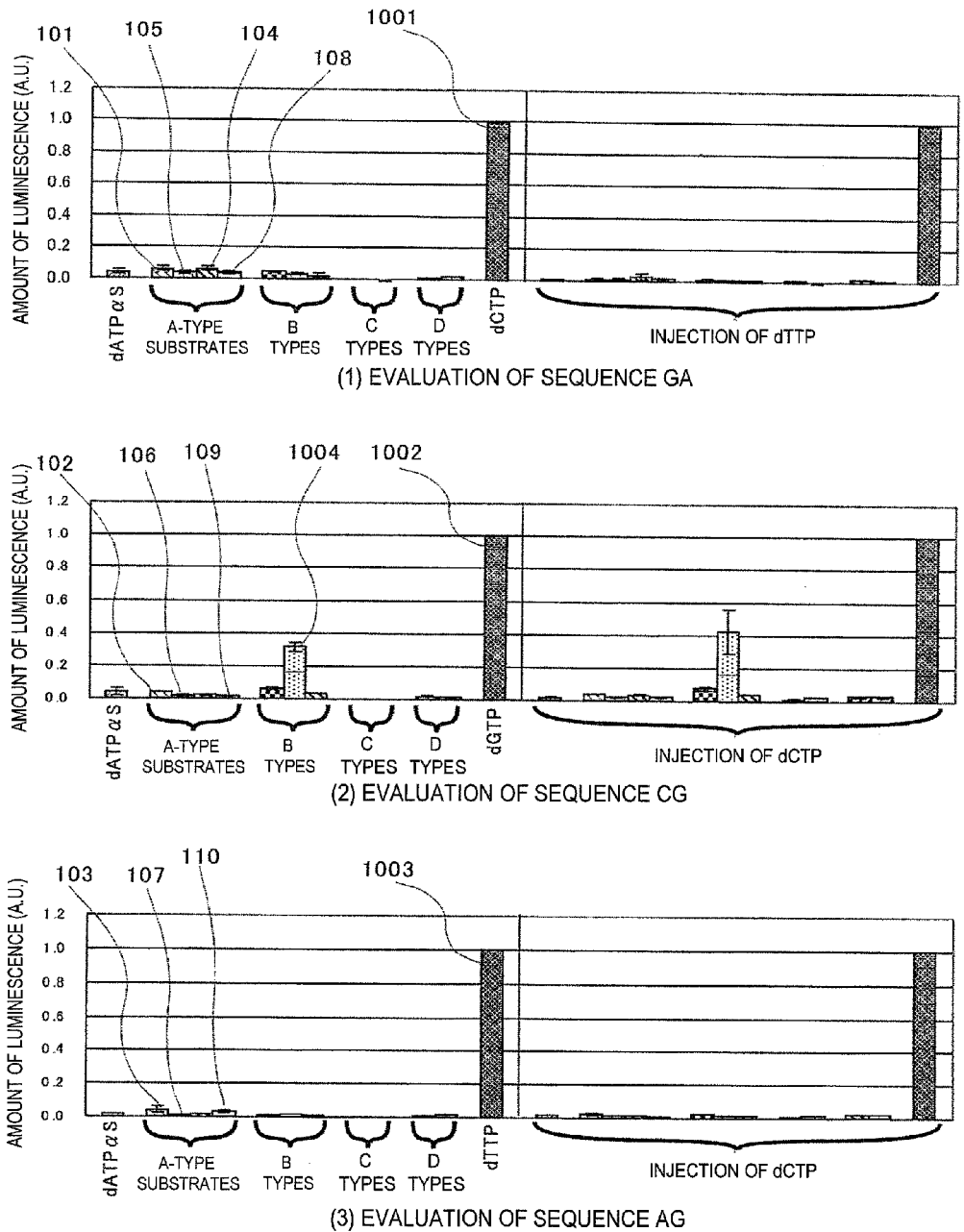
FIG. 10 is graphs showing the results of evaluating exclusivity between the respective synthetic substrates and the other nucleotides (G, C, and A).

Next, with regard to the respective synthetic substrates, the exclusivity of the other nucleotides (G, C, and A) was assessed using each of Sequence GA, Sequence CG, and Sequence AG and the primer. FIG. 10 shows the results. The respective amounts of luminescence were determined by normalizing the amounts of luminescence by using substrates dCTP 1001, dGTP 1002, and dTTP 1003, which had an affinity to Sequence GA, Sequence CG, and Sequence AG, respectively, as 1. In addition, a background luminescence component of the respective substrates was compensated by taking its difference into account in a manner similar to that of the preceding figures.

These results revealed the following. In respect to A-type compounds, A3a exhibits luminescence for all the three kinds of nucleotides (101, 102, and 103). However, A3c exhibits a little poor exclusivity of nucleotide G (104), but is generally good. Nucleotides A3b (105, 106, 107) and A3d (108, 109, 110) have excellent exclusivity, and are better than dATPαS of a conventional technique. Both the nucleotides A3b and A3d are "compounds whose 7-position of a purine group is modified by a substituent having a basic aromatic substituent via an ethenyl group (a C—C double bond) as a substituent". B-type compounds have a little lower exclusivity of nucleotide C. Although B4 exhibits luminescence (1004), they are generally good. C-type and D-type compounds are found to have good exclusivity. With regard to the D-type compounds, as described previously, the nucleotide elongation ability by itself can be presumed to be low because of a poor affinity even for nucleotide T.

Figure 11:
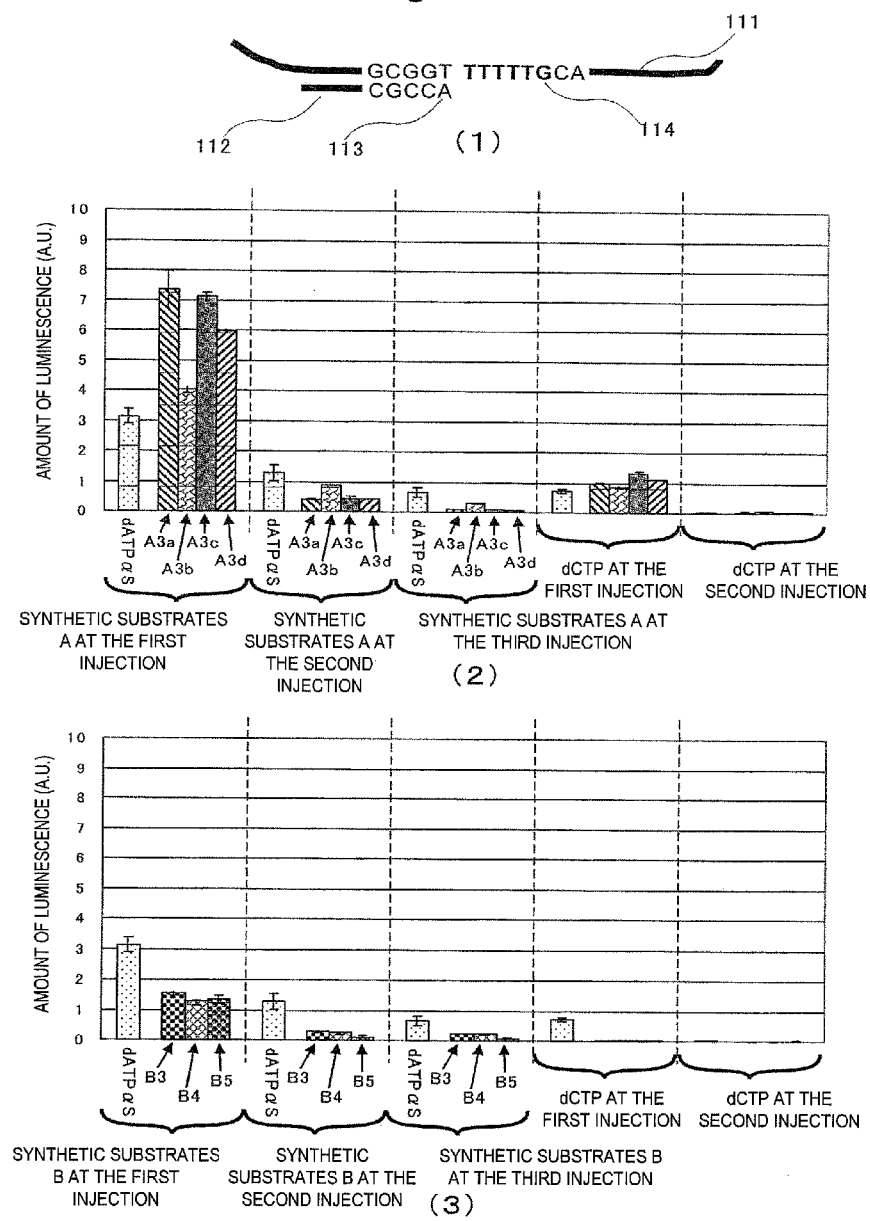
FIG. 11 is graphs showing the results of evaluating an ability of incorporation of the respective synthetic substrates into consecutive nucleotides of T.

Next, by using Sequence 5T, the ability of incorporation of the respective synthetic substrates into consecutive nucleotides of T was evaluated by the following procedure. The reaction reagent was prepared by using Sequence 5T as a target oligo in the same manner as in the case of evaluation of elongation of one nucleotide as described before. In this case, a target oligo 111 and a primer 112 form a complementary strand binding as depicted in FIG. 11(1). Due to the above, when dATP is dispensed into this reaction reagent as a substrate, five molecules of the substrate are consecutively elongated per target molecule as a primer having the substrate at the 3' end 113, thereby releasing five molecules of pyrophosphate. If the elongation for all the five nucleotides is not completed, a portion of the nucleotide T remains in a single-stranded state. Because of this, when substrate dATP is dispensed again, the portion is elongated only in the case where a portion of incomplete elongation remains. Therefore, the release of pyrophosphate can be detected as luminescence. Here, in order to evaluate the ability of continuous elongation of the respective synthetic substrates toward consecutive nucleotides, synthetic substrates (the final concentration was 2 μM) to be added to the reaction reagent were dispensed three consecutive times. In addition, substrate dCTP, which is complementary to nucleotide G 114, was subsequently dispensed twice to detect luminescence. Then, whether or not continuous elongation occurred was examined while keeping a state in which an amount of five nucleotides of the synthetic substrate had been incorporated. FIG. 11(2) and FIG. 11(3) show the results. FIG. 11(2) shows the results of evaluating A-type synthetic substrates. In addition, FIG. 11(3) shows the results of evaluating B-type synthetic substrates. In the ordinate, the amount of luminescence was normalized as follows: first, dATP was used as a substrate for elongation; next, dCTP was used to carry out elongation of a strand complementary to nucleotide G; then, the amount of luminescence due to the elongation by dCTP incorporation was normalized as 1.

These results have lead to the following. First, in the case of elongation using substrate dATPαS, luminescence derived from incomplete elongation was detected even at the third injection. That is, a problem has been found that dATPαS of a conventional technique causes incomplete elongation at the time of elongation requiring continuous incorporation. In contrast, in the evaluations using four kinds of the A-type synthetic substrates, luminescence derived from the incomplete elongation still appeared at the time of the second injection. However, the amount of the luminescence was lower than that of the case of dATPαS. Furthermore, at the time of the third injection, almost no luminescence derived from the incomplete elongation appeared. Because of this, it has been found that by the time of the second reaction, elongation of a portion having 5 consecutive nucleotides of T has been completed. In addition, regarding the signal at the time of the subsequent dCTP injection, one nucleotide equivalent of elongation was detected. This demonstrates that the A-type synthetic substrates sufficiently function as a substitute for dATP. In contrast, FIG. 11(3) indicates that the B-type compounds did not completely execute continuous incorporation. Specifically, the amount of luminescence at the time of the B-type substrates injection was low, and no luminescence at the time of the following dCTP injection was able to be observed. These results have lead to a conclusion that there is almost no complete complementary strand elongation in respect to one having the 5 consecutive nucleotides of T among the target oligos. The results have been obtained that the A-type synthetic substrates are suitable as a substitute for dATP.

Figure 13:
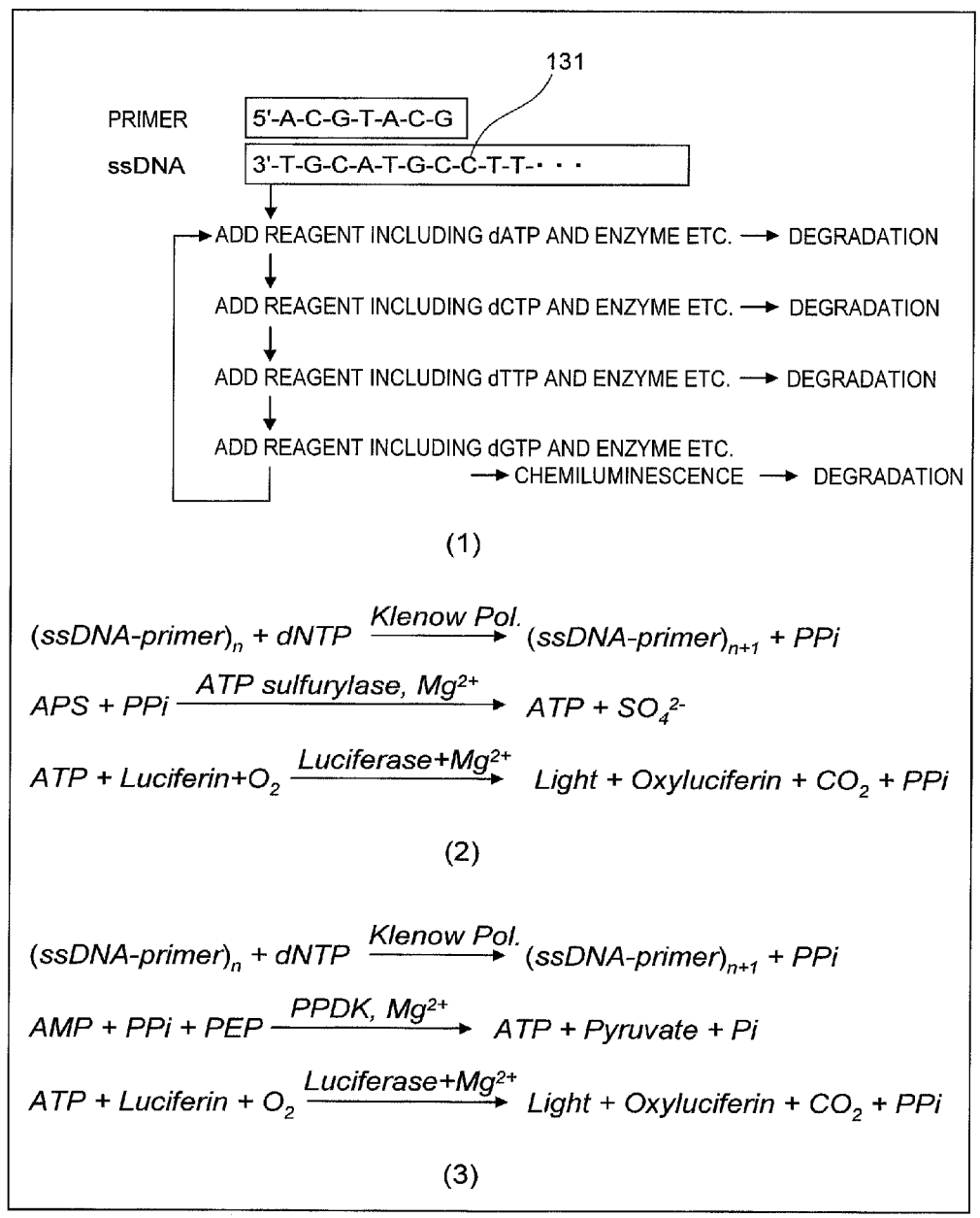
FIG. 13 is a diagram showing a procedure for a sequencing method using a stepwise chemical reaction represented by pyrosequencing.
Figure 14:
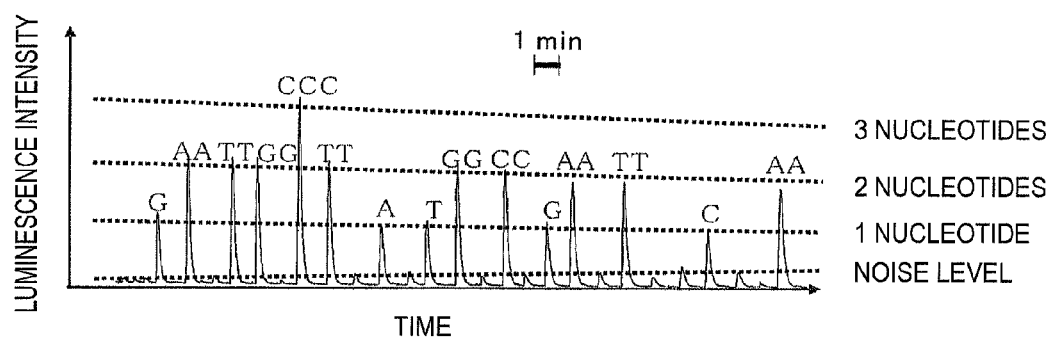
FIG. 14 is a diagram showing luminescence for each substrate injection. Of note is addition of the substrates in the order of A, C, T, and G.

Next, the amount of the substrate dispensed was doubled (the final concentration was 4 μM), and similar experiments were carried out. By doubling the dispensed amount of the substrate, a phenomenon has been found that incomplete elongation is somewhat alleviated. The reason is described below. As indicated in FIGS. 13(2) and 13(3), in a sequencing method using a stepwise chemical reaction, substrate incorporation into a target DNA and substrate degradation by apyrase are competed in a reaction reagent. The incomplete elongation phenomenon occurs because the substrate is degraded before completion of the elongation when a large amount of the nucleotides is required like in the case of the consecutive nucleotides. Consequently, as the injected amount of the substrate increases, the required time for the substrate degradation increases, which is likely to fulfill the substrate. However, an increase in the substrate amount causes an increase in the burden of the substrate degradation. An undegraded substrate is likely to remain, which causes a new problem (e.g., reading the next sequence). Usually, under reagent conditions used by the present inventors, the injected substrate suitably has the final concentration of about 2 to 4 μM. The injection having the above concentration or more causes the undegraded substrate to remain. Because of this, it is ideal that the final concentration should be kept at 4 μM or less, and that just one injection makes the elongation completed. FIG. 12 shows the results of this experiment. These results have lead to the following. First, with regard to elongation using a substrate dATPαS, luminescence derived from incomplete elongation was detected at the third injection even if the substrate amount was doubled. Because of this, it is found impossible for dATPαS of a conventional technique to circumvent a problem of the incomplete elongation at the time of elongation of 5 consecutive nucleotides. In contrast, examinations of using A-type synthetic substrates demonstrated that luminescence derived from incomplete elongation was able to be made low at the time of the second injection. That is, the A-type compounds were said to be able to complete 5-consecutive-nucleotide elongation only by the first injection. Here, a rate of incomplete elongation E is defined as the following equation. The rates of incomplete elongation for the respective substrates are listed in Table 2.

The rate of incomplete elongation after the first injection ($E1$)=(the amount of luminescence for the second and third injections)/(the total amount of luminescence for the first to third injections).

The rate of incomplete elongation after the second injection ($E2$)=(the amount of luminescence at the third injection)/(the total amount of luminescence for the first to third injections).

TABLE 2

Rate of Incomplete Elongation for 5 Consecutive Nucleotides

| Substrate Name | Rate of Incomplete Elongation after the First Injection (%) | Rate of Incomplete Elongation after the Second Injection (%) |
| --- | --- | --- |
| dATPαS | 36.8 ± 7.8 | 13.6 ± 5.1 |
| A3a | 3.8 ± 0.8 | 1.2 ± 0.2 |
| A3b | 11.2 ± 2.9 | 2.2 ± 0.3 |
| A3c | 3.0 ± 0.2 | 1.1 ± 0.1 |
| A3d | 3.5 ± 0.1 | 1.0 ± 0.0 |

These results demonstrate that the rate of incomplete elongation for A-type compounds after the first injection was 15% or less. In particular, with regard to the three kinds of A3a, A3c, and A3d, the rates of incomplete elongation after the first injection were 4% or less. In addition, when the three kinds of A3a, A3c and A3d were dispensed twice, the rates of incomplete elongation were able to be decreased to about 1%. Also, when A3b was dispensed twice, the rate of incomplete elongation was able to be decreased to about 2%. These results demonstrated that the elongation inhibition in the case of using dATPαS, which had been a conventional problem, was able to be solved by using a synthetic substrate of an embodiment of the present invention. In addition, FIG. 12(2) revealed that B-type substrates certainly had a problem during continuous elongation.

In view of the above, A-type compounds, specifically "compounds whose 7-position of a purine group is modified by a substituent via an ethenyl group (a C—C double bond)" are found to reduce background luminescence to a practical level and to be effective as a substrate substitute for dATP, the substitute having a better elongation ability at the time of continuous incorporation. In particular, A3d exhibited better characteristics in all the examinations.

Figure 15:
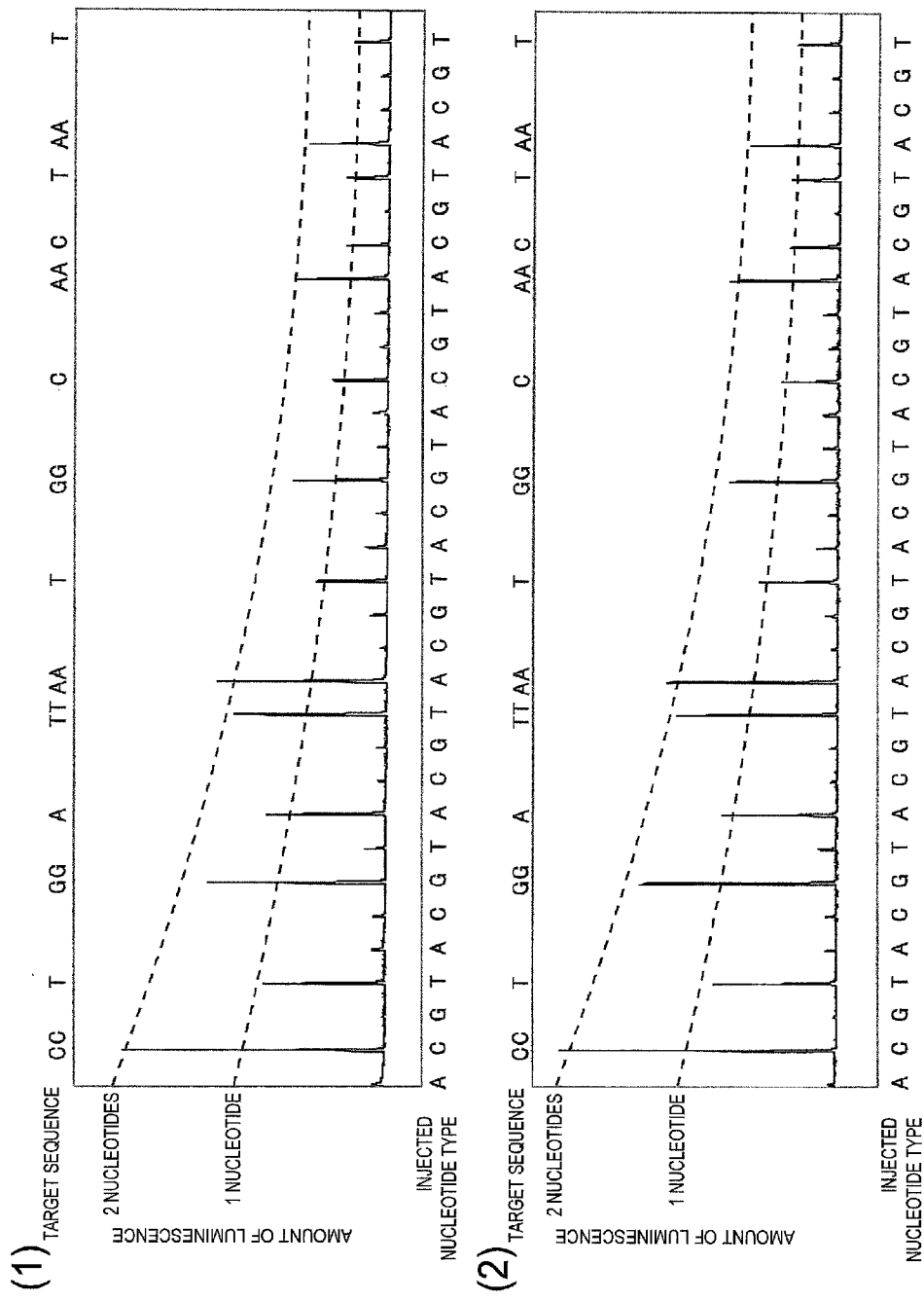
FIG. 15 is diagrams showing the results of comparing use between synthetic nucleotide A3d and dATPαS as a substitute for dATP in a sequencing method using a stepwise chemical reaction. In diagram (1), the synthetic substrate A3d is used as a substitute for dATP. In diagram (2), the synthetic substrate dATPαS is used as a substitute for dATP.

Next, by using the developed substrates, nucleotide sequences were analyzed. FIG. 15 is pyrograms showing the results of sequence analysis using synthetic nucleotide A3d as a substitute for dATP in a sequencing method using a stepwise chemical reaction. The analyzed oligo Sequence S1 and a primer S2 are described below.

```
Sequence S1 (SEQ ID NO: 7):
gatttgggat agaggagcat tagttgccat taatccaggg tgcatgctgg tacttcaaca Sequence P2 (SEQ ID NO: 8)
tgttgaagta ccagcatgca c
```

Of note is that the Sequence P2 represents a primer sequence. This primer can complementarily bind to the underlined portion of the above Sequence S1. In addition, reagent conditions used for the sequence analysis were designated in Condition 3 of Table 1.

FIG. 15(1) shows the case of using substrate A3d (the final concentration was 2 µM). In addition, for comparison, FIG. 15(2) shows the case of using dATPαS (the final concentration was 2 µM) of a conventional technique. At the bottom of each diagram, the injected nucleic acid substrate species (the injected nucleotide type) were designated. Among the species, the substrate represented by "A" is A3d in (1) and dATPαS in (2), respectively. Also, at the top, nucleotide types which were incorporated in this oligo were designated. Specifically, the nucleotide types represent a complementary strand sequence that is an upstream sequence of the portion (the underlined portion of the Sequence S1) which complementarily binds to the primer P2. For example, the nucleotide attached to the 3' end of the primer P2 is located to the next left of the underlined portion of the Sequence S1, and corresponds to 2 consecutive nucleotides of G. Accordingly, its complementary strand sequence has 2 consecutive nucleotides of C, and the sequence "CC" is thus the start sequence as illustrated in FIG. 15. In addition, the broken lines represent standard values which convert the amount of the resulting luminescence into the number of nucleotides. For example, with regard to the above "CC", the amount of luminescence equivalent to two nucleotides was observed. From this result, two nucleotides of C were found to be incorporated. FIG. 15 demonstrates that both a substrate of an embodiment of the present invention and dATPαS of a conventional technique can be used for a nucleotide sequence analysis in respect to the oligo of analysis object in this experiment. This oligo contains consecutive nucleotides having maximum two nucleotides, so that both the substrates exhibited no difference. However, A3d has a better ability of incorporation into consecutive nucleotides than dATPαS, and seemed to be effective in analyzing a sample having consecutive nucleotides of T.

Therefore, a sequence having 3 consecutive nucleotides of T was analyzed for comparison. Analyzed DNA Sequence S2 and a primer P3 are described below.

```
DNA Sequence S2 (SEQ ID NO: 9):

tgttgaagta ccagcatgca ccatggggga cgctgctcat cttcttaaag atttgatttt tctcccataa aatgtttttt ctctttctgg taggacaaat attggcaaat ttgacatgat ttgggataga ggagcattag ttgccattaa tccaggtgat cgcaaatggt aagtaatttt Sequence P3 (SEQ ID NO: 10):
taatggcaac taatgctcct
```

Of note is that Sequence P3 represents a primer sequence. This primer can complementarily bind to the underlined portion of the above DNA Sequence S2. FIGS. 16 to 20 show the results of a sequence analysis. In addition, the reagent conditions were listed together in the following Table 3.

TABLE 3

| Luminescence Reagent Composition (used PPDK) | |
|---|---|
| Composition | Luminescence Reagent Condition 4 |
| Tricine | 25 mM |
| EDTA | 0.5 mM |
| Mg-Acetate | 5 mM |
| DTT | 0.5 mM |
| PPDK | 33.8 U/mL |
| Luciferase | 523 GLU/mL |
| Luciferin | 0.4 mM |
| AMP | 0.4 mM |
| Apyrase | 1 U/mL |
| PEP | 0.08 mM |

In this experiment, an enzyme system which converts PPi into ATP has employed an enzyme system in which PPi and AMP are converted into ATP by PPDK as described in the conventional technique (Patent Literature 4). The items of the figure are identical to those of FIG. 15. At the bottom of the respective figures, the injected nucleotide types are designated. At the top, the nucleotide types which have been incorporated into a complementary DNA sequence of analysis object are designated. The substrate was injected in the order of "bases A, T, C, and G", and 7 cycles were analyzed. As indicated in the target sequence, in this analysis, two regions (Cycle 4 and Cycle 7) having 3 consecutive nucleotides of A incorporated are present. Because of this, a difference in the ability of continuous incorporation of a nucleic acid substrate that is used as a nucleotide A can be assessed. Hereinafter, the details are described.

Figure 16:
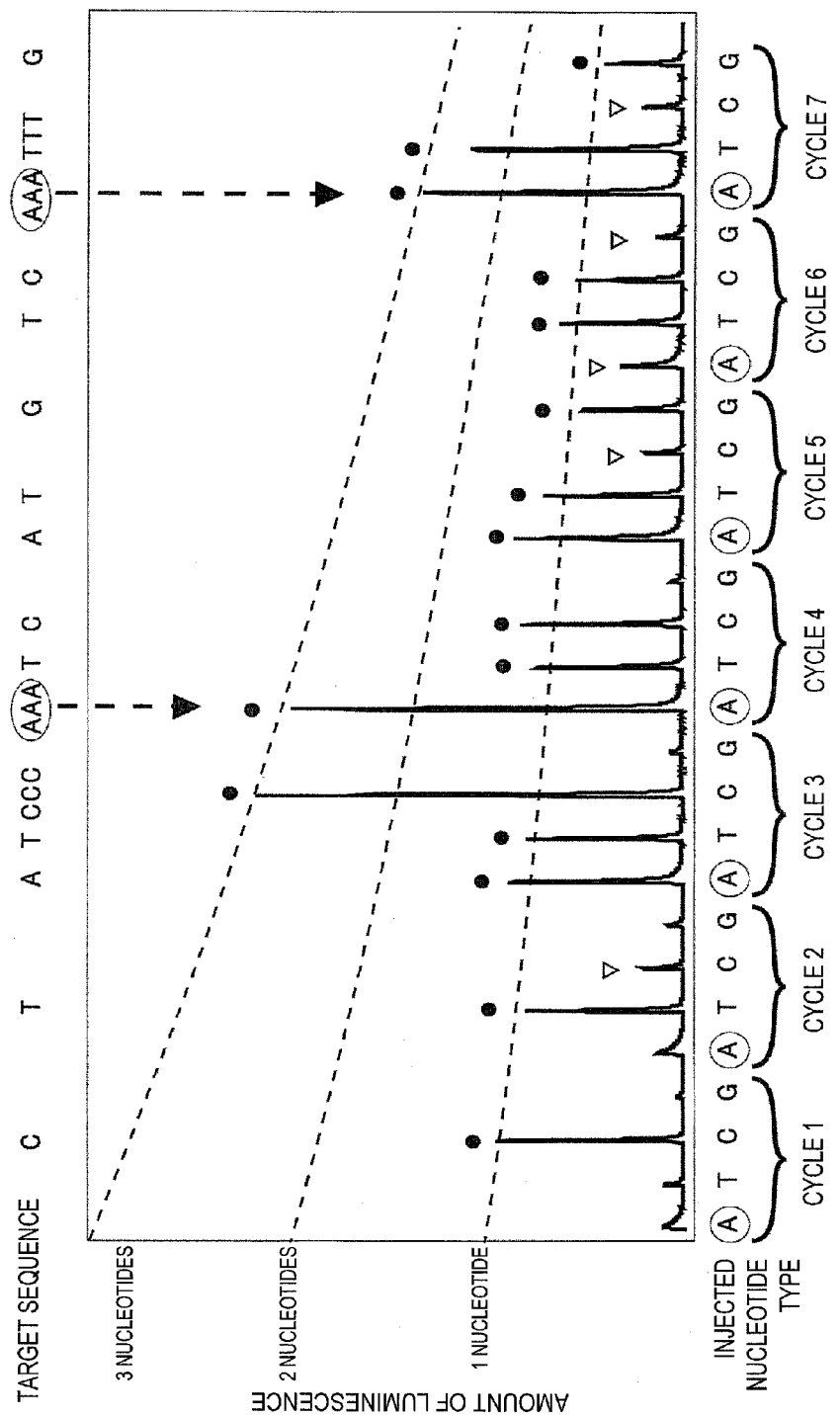
FIG. 16 is a diagram showing the sequence analysis results in the case of using synthetic nucleotide A3d (the final concentration is 2 μM) as a substitute for dATP. In this case, the synthetic substrate A3d (the final concentration is 2 μM) is used as a substitute for dATP.
Figure 17:
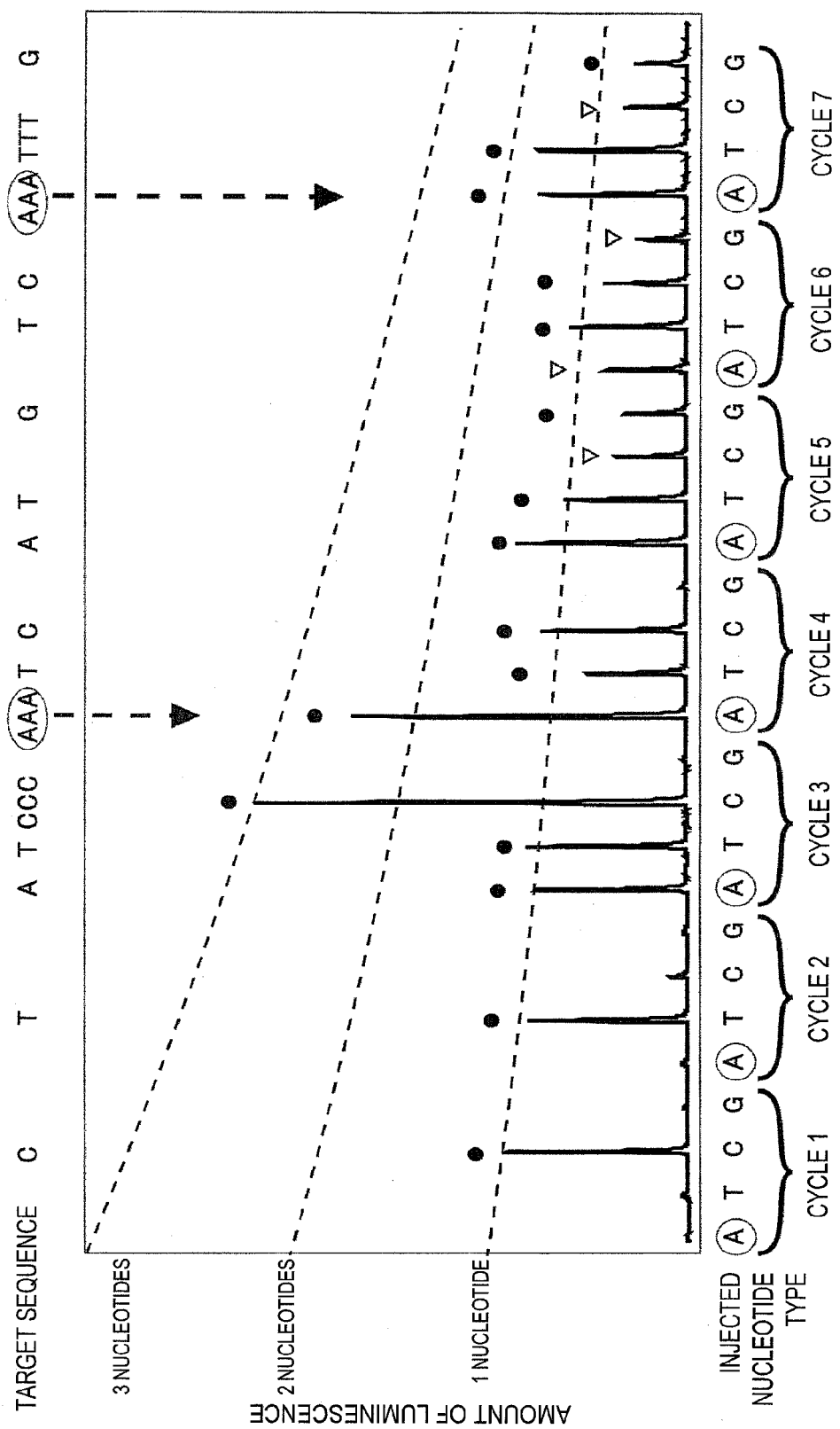
FIG. 17 is a diagram showing the sequence analysis results in the case of using substrate dATPαS (the final concentration is 2 μM) as a substitute for dATP. In this case, the dATPαS (the final concentration is 2 μM) is used as a substitute for dATP
Figure 18:
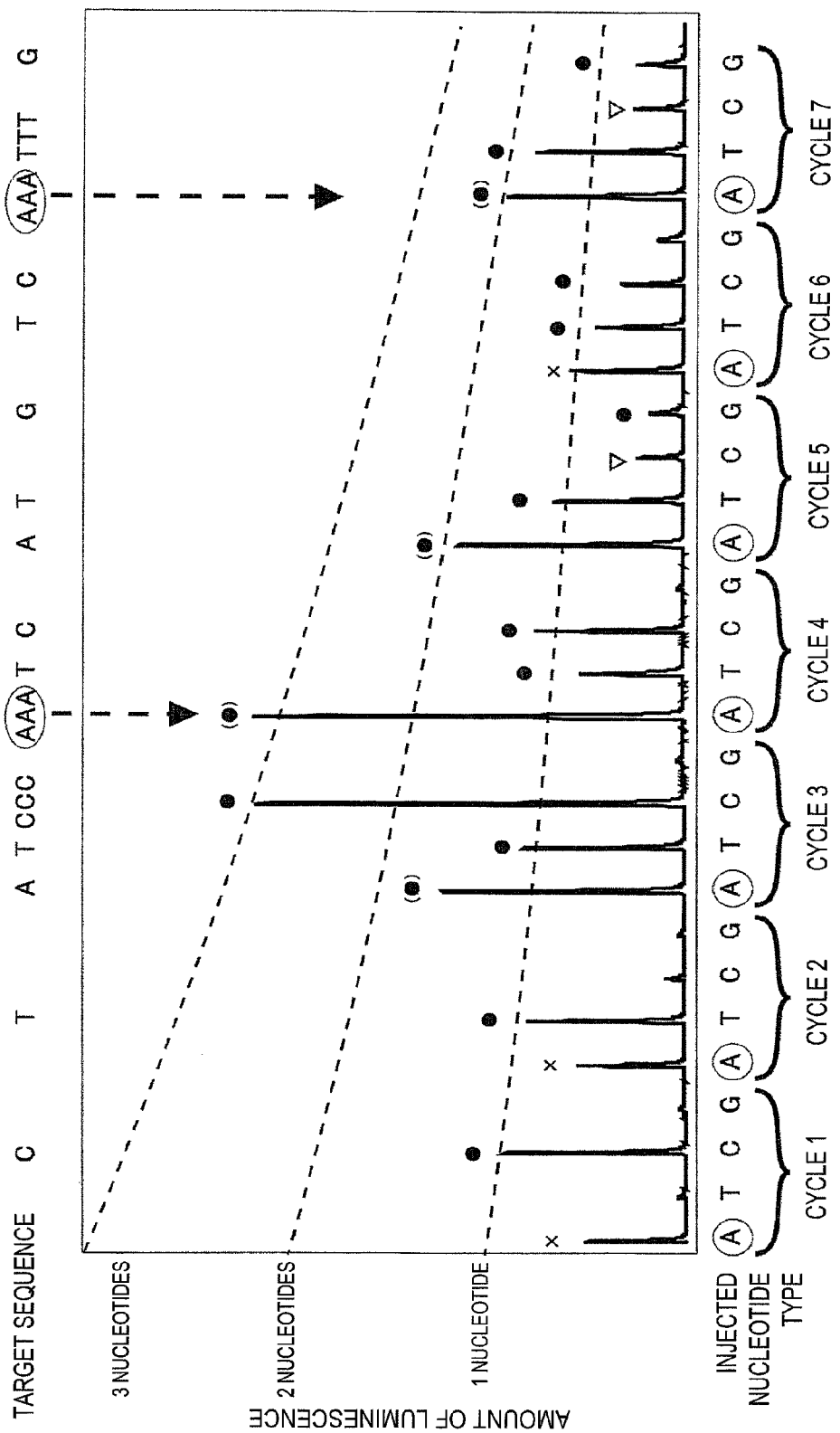
FIG. 18 is a diagram showing the sequence analysis results in the case of using substrate C$^7$dATP (the final concentration is 2 μM) as a substitute for dATP. In this case, the C$^7$dATP (the final concentration is 2 μM) is used as a substitute for dATP

First, three kinds of the substrates (A3d, dATPαS, and $C^7$dATP) having the final concentration of 2 μM were used. The results of a sequence analysis will be described (FIGS. 16 to 20). FIG. 16 shows the results of a sequence analysis using a substrate A3d (the final concentration was 2 μM) of an embodiment of the present invention. At the time of dispensing A (surrounded by the circle ○) which represented the injected nucleotide type, A3d was used. The substrate A3d, as described in the preceding experiment (FIG. 7), exhibited a substrate specificity having about one order higher than that of dATPαS. Accordingly, as the signal corresponding to A at the first cycle indicated, background luminescence was observed. Due to this phenomenon, the luminescence signal corresponding to nucleotide A constantly included the increased background luminescence. The symbol • in the figure denotes elongation luminescence corresponding to a nucleotide sequence of a sample. In contrast, the major luminescence without corresponding to the nucleotide sequence is represented by the symbol ∇. FIG. 17 similarly shows the results of a sequence analysis using a substrate ATPαS (the final concentration was 2 μM) in a similar manner. At the time of dispensing A (surrounded by the circle ○) which represented the injected nucleotide type, dATPαS was used. The resulting pyrogram and the nucleotide sequence of a sample were compared. The symbol • in the figure denotes elongation luminescence corresponding to a nucleotide sequence of a sample. In contrast, the major luminescence without corresponding to the nucleotide sequence is represented by the symbol ∇. FIG. 18 similarly shows the results of a sequence analysis using a substrate $C^7$dATP (the final concentration was 2 μM) in a similar manner. At the time of dispensing A (surrounded by the circle ○) which represented the injected nucleotide type, $C^7$dATP was used. The substrate $C^7$dATP, as described in the preceding experiment (FIG. 7), exhibited a substrate specificity having about two orders higher than that of dATPαS. Accordingly, as the signal corresponding to A at the first cycle indicated, big background luminescence was observed. Due to this phenomenon, the luminescence signal corresponding to nucleotide A constantly included the increased background luminescence. The symbol x in the figure denotes just a background luminescence signal. The symbol • denotes elongation luminescence corresponding to a nucleotide sequence of a sample. However, the symbol (•) denotes inclusion of both elongation-derived luminescence and background luminescence. In contrast, the major luminescence without corresponding to the nucleotide sequence is represented by the symbol ∇.

Comparison among FIGS. 16 to 18 has lead to the following. First, regarding a difference in the ability of 3-consecutive-nucleotide incorporation at Cycle 4, the following points are included. (1) In the experiment using dATPαS (FIG. 17), an elongation signal for the 3 consecutive nucleotides at Cycle 4 decreased, so that incomplete elongation was able to be presumed to occur. As a result, the signals for a nucleotide T at Cycle 4 and a nucleotide G at Cycle 5 decreased. Further, a decrease in signals for 3 consecutive nucleotides A and T at Cycle 7 occurred. (2) In contrast, in the experiment using A3d (FIG. 16), some noise signals ∇ were observed. However, up to the nucleotide G at Cycle 7, a sequence analysis was found to be able to be definitely carried out. (3) In addition, in the experiment using $C^7$dATP (FIG. 18), substrate-derived background luminescence was large, so that the precise sequence identification was found to be difficult. Also, the signals which seemed to result from insufficient elongation were observed, including the nucleotide G at Cycle 5 and the following nucleotide A (3 consecutive nucleotides) at Cycle 7.

Figure 19:
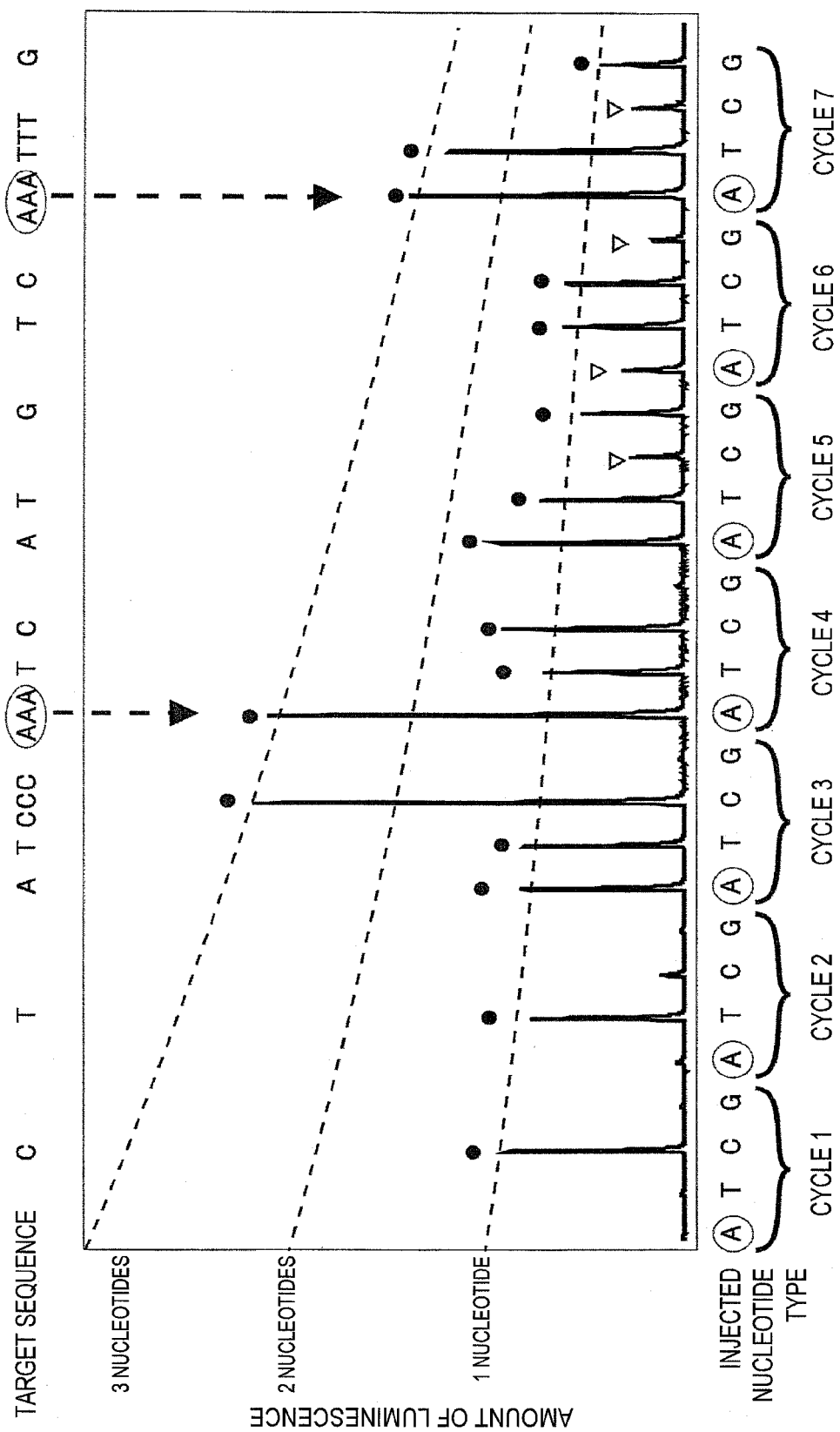
FIG. 19 is a diagram showing the sequence analysis results in the case of using substrate dATPαS (the final concentration is 4 μM) as a substitute for dATP. In this case, the dATPαS (the final concentration is 4 μM) is used as a substitute for dATP
Figure 20:
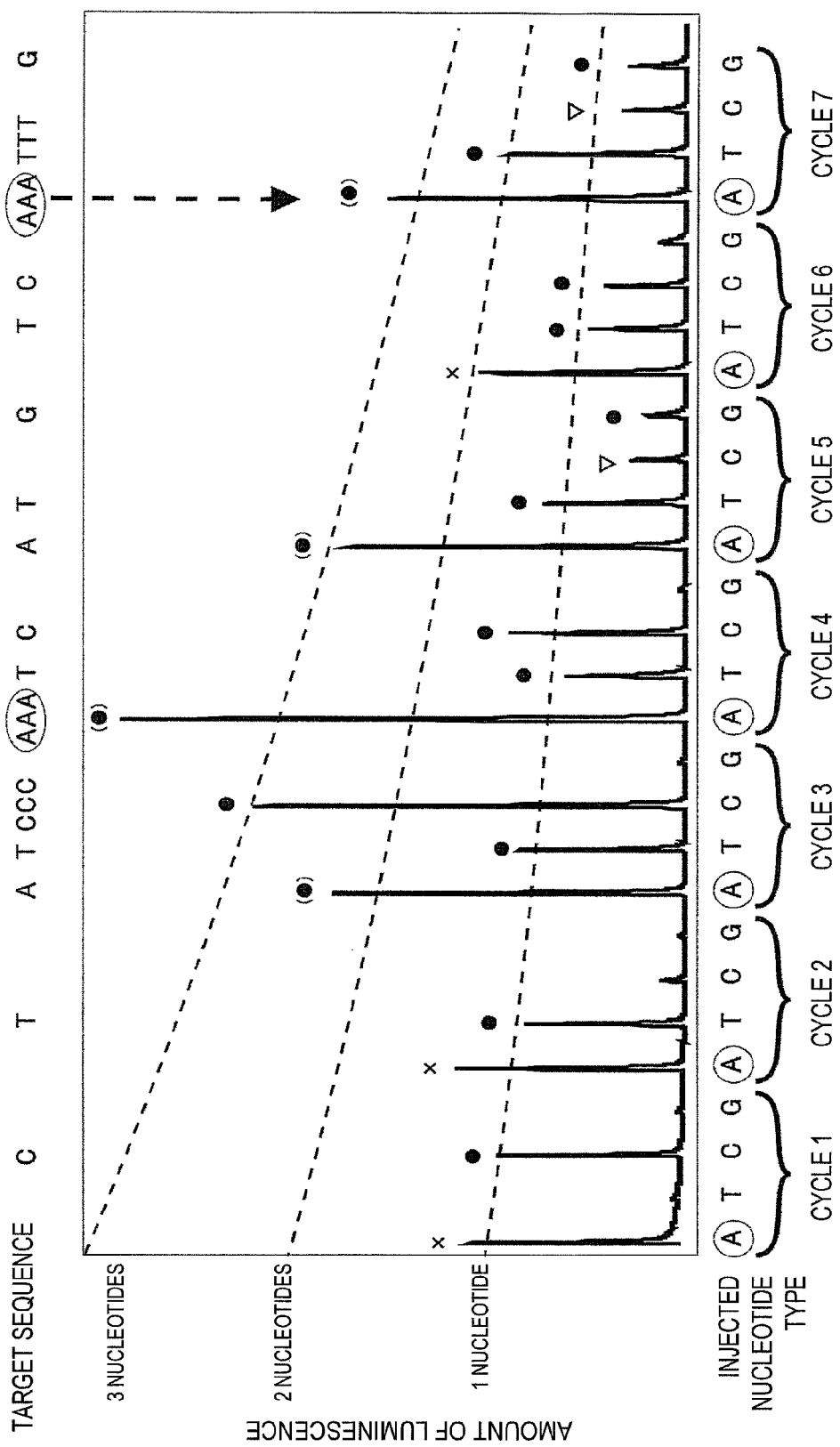
FIG. 20 is a diagram showing the sequence analysis results in the case of using substrate C$^7$dATP (the final concentration is 4 μM) as a substitute for dATP. In this case, the C$^7$dATP (the final concentration is 4 μM) is used as a substitute for dATP.

As described above, with regard to the experiments using dATPαS and $C^7$dATP, it has been found that dATPαS has a problem of incorporation of consecutive nucleotides and $C^7$dATP has a problem of poor precision due to high background luminescence. In addition, with regard to $C^7$dATP, a decrease probably due to incomplete elongation was observed after Cycle 5. Because of that, in respect to the above two kinds of the substrates, the final concentration of the substrates was doubled (4 μM) only for the nucleotide A to carry out the experiments. FIGS. 19 and 20 show the experimental results of a reaction of dATPαS and $C^7$dATP at the final concentration of 4 μM, respectively. These results have lead to the following.

FIG. 19 demonstrates that doubling the amount of dispensed dATPαS can improve incomplete elongation. However, since the signal corresponding to the nucleotide A at Cycle 5 approaches the amount of about two-nucleotide equivalent, the incomplete elongation is not completely resolved. Accordingly, the amount caused by the incomplete elongation seems to be included in the signal corresponding to the nucleotide A at Cycle 5 in a certain degree. In addition, in FIG. 20, the results of doubling the amount of $C^7$dATP showed that incomplete elongation for the nucleotide G at Cycle 5 was not improved. Also, the background luminescence was proportional to the substrate amount, and thus was doubled. As a conclusion, the better results were not achieved.

In view of the above, for the phenomenon of continuous incorporation, it has been demonstrated that a nucleic acid substrate of an embodiment of the present invention is effective.

INDUSTRIAL APPLICABILITY

The present invention is applicable to nucleic acid substrate reagents for a sequencing method using a stepwise chemical reaction utilizing luciferase luminescence among gene sequence analyses. The sequencing method using a stepwise chemical reaction utilizing luciferase luminescence can perform an analysis without using an excitation light, so that the method has been applied to a small simplified analyzer and a large-scale parallel analyzer. A substance of an embodiment of the present invention is available for these analyzers. In addition, the present invention can be applied to a DNA chip technique using a labeled target or a polymorphism analysis technique using one nucleotide elongation, etc.

REFERENCE SIGNS LIST

81: Target (nucleic acid sample), 82: Primer, 83: Nucleotide A, 84: Nucleotide T, 85: Nucleotide G, 812: Luminescence in the case of using A3a, 813: Luminescence in the case of using A3b, 814: Luminescence in the case of using A3c, 815: Luminescence in the case of using A3d, 822: Amount of luminescence at the time of dispensing dCTP following A3a, 823: Amount of luminescence at the time of dispensing dCTP following A3b, 824 Amount of luminescence at the time of dispensing dCTP following A3c, 825: Amount of luminescence at the time of dispensing dCTP following A3d, 91: Profile of dATPαS, 92: Profile of A3c, 101-103: Amount of luminescence in the case of using A3a, 104: Amount of luminescence in the case of using A3c, 105-107: Amount of luminescence in the case of using A3b, 108-110: Amount of luminescence in the case of using A3d, 1001-1003: Amount of luminescence in the case of using dCTP, 1004: Amount of luminescence in the case of using B4, 111: Target oligo, 112: Primer, 113: the 3' end of primer, 114: Nucleotide G, 131: Nucleotide C.

All the publications, patents, and patent applications which have been cited in the specification of the present application are herein incorporated by reference in their entirety.

The invention claimed is:

1. A compound selected from the following:

[Chemical Formula 1]

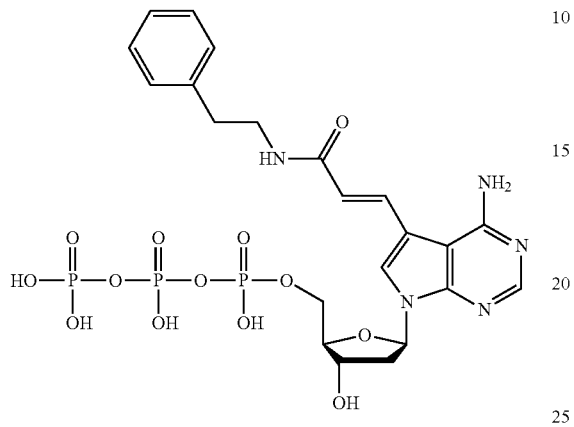

A3a

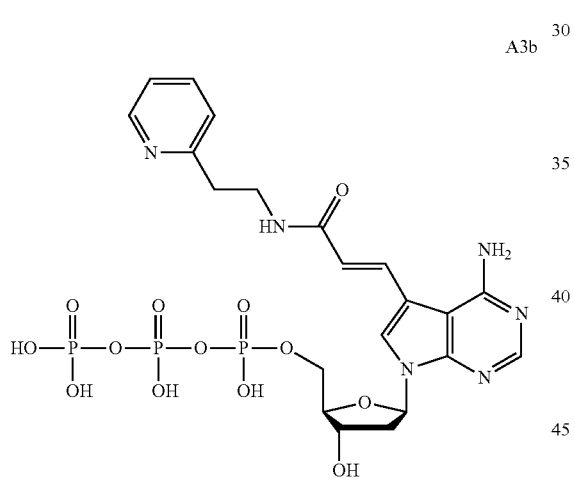

A3b

A3c

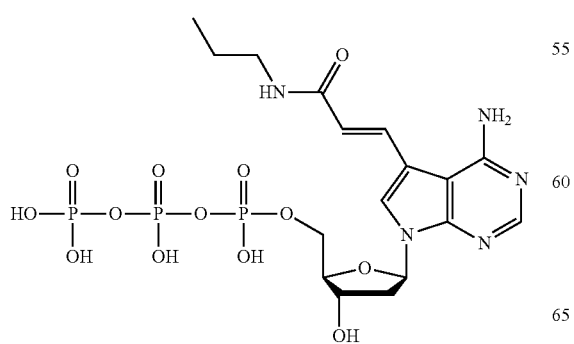

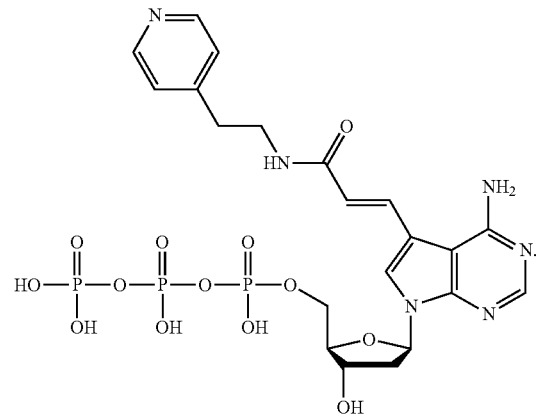

A3d

2. A compound represented by the following formula:

[Chemical Formula 2]

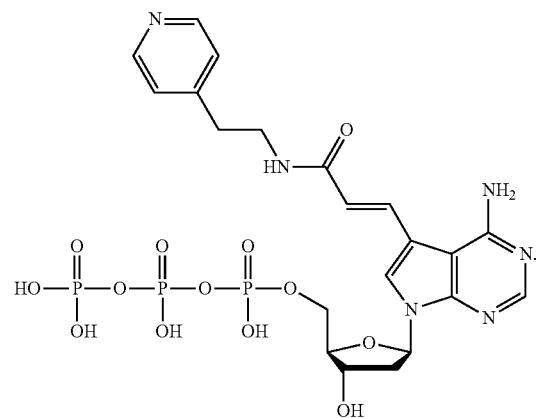

A3d

3. A method for nucleic acid analysis, comprising the steps of:
  carrying out a complementary-strand synthesis by using a nucleic acid sample as a template and by adding complementary nucleic acid substrates for nucleotides A, G, T, and C;
  generating ATP from pyrophosphate generated in the complementary-strand synthesis by using an enzyme; and
  determining the presence or absence of the complementary-strand synthesis by detecting chemiluminescence produced in a luciferase reaction,
  wherein a 7-substituted deoxyribonucleotide triphosphate whose nitrogen at the 7-position of a purine group is substituted by a carbon modified by a substituent is used as the complementary nucleic acid substrate for nucleotide T, and
  wherein the 7-substituted deoxyribonucleotide triphosphate is selected from the group consisting of 39
A3a
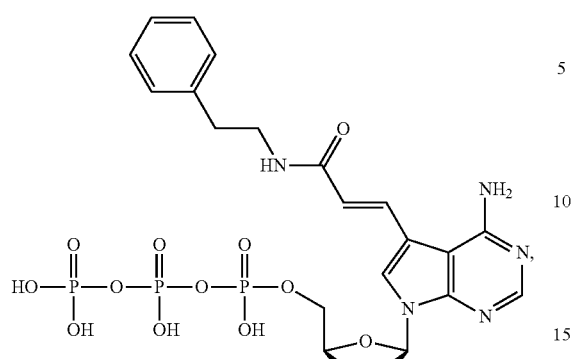
A3b
A3c
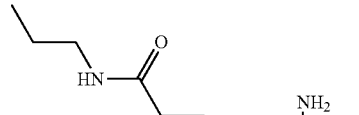
and
40
4. The method for nucleic acid analysis according to claim 3, wherein the 7-substituted deoxyribonucleotide triphosphate is a compound represented by the formula:
A3d
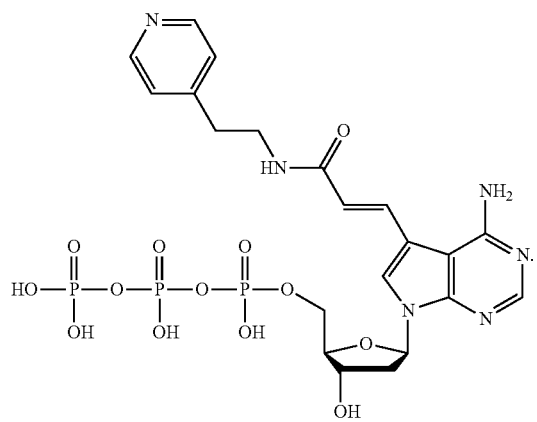
5. A complementary nucleic acid substrate reagent for nucleotide T, comprising a 7-substituted deoxyribonucleotide triphosphate from the group consisting of
A3a
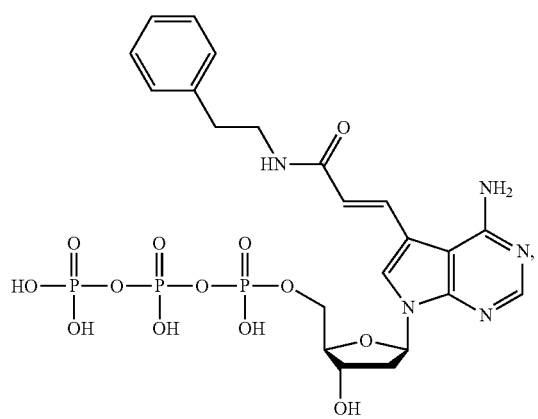
A3b
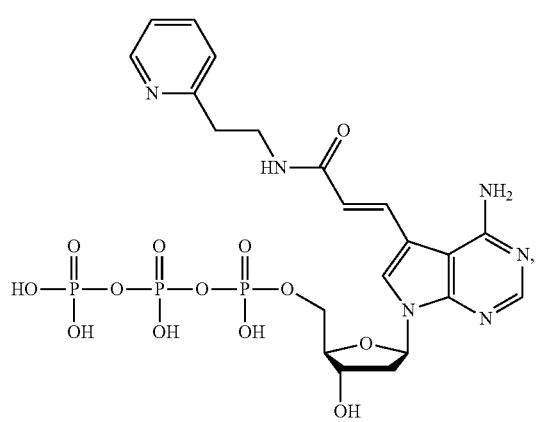

-continued
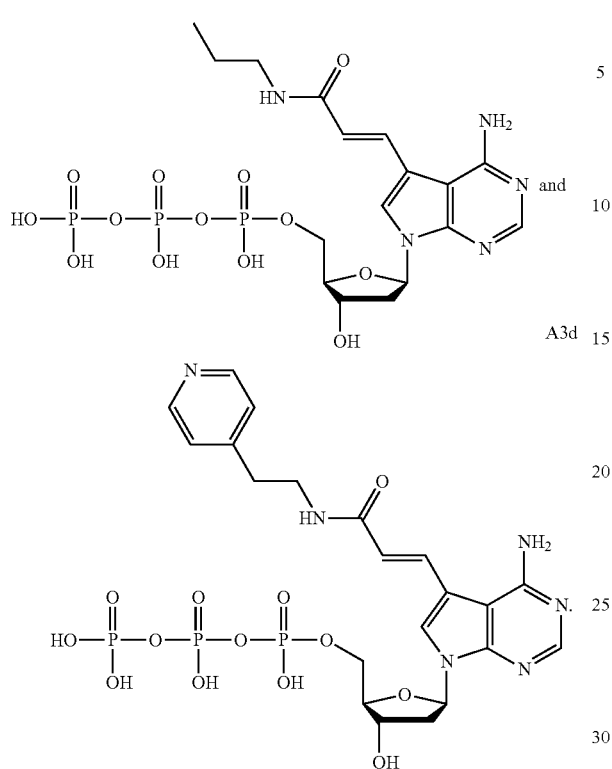
6. The reagent according to claim 5, wherein the 7-substituted deoxyribonucleotide triphosphate is a compound represented by the formula:
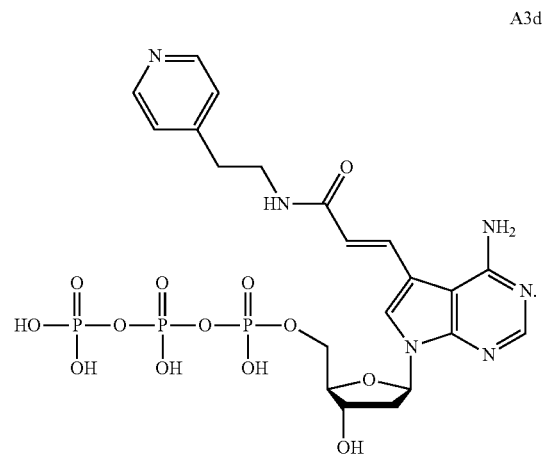
* * * * *